(12) United States Patent
Buechler et al.

(10) Patent No.: US 6,238,931 B1
(45) Date of Patent: *May 29, 2001

(54) FLUORESCENCE ENERGY TRANSFER IN PARTICLES

(75) Inventors: Kenneth F. Buechler, San Diego; Joseph Barry Noar, Solana Beach; Lema Tadesse, San Diego, all of CA (US)

(73) Assignee: Biosite Diagnostics, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/274,534

(22) Filed: Jul. 12, 1994

Related U.S. Application Data

(63) Continuation-in-part of application No. 08/138,708, filed on Oct. 18, 1993, now abandoned, and a continuation-in-part of application No. 08/126,367, filed on Sep. 24, 1993, now abandoned.

(51) Int. Cl.[7] .................. G01N 33/533; G01N 33/546; G01N 33/552; C07K 17/08
(52) U.S. Cl. .................. 436/546; 435/6; 436/525; 436/527; 436/528; 436/531; 436/534; 530/389.2; 530/391.3; 530/811; 530/812; 530/815; 530/818; 530/402

(58) Field of Search .................. 435/6, 7.1, 7.5, 435/7.92; 436/518, 528, 529, 520, 531, 546, 800, 527, 525, 534; 427/213.34, 157; 428/402.24, 407; 252/301.34, 301.35; 530/389.2, 818, 391.3, 811, 815, 812, 402

(56) References Cited

FOREIGN PATENT DOCUMENTS

| | | |
|---|---|---|
| 0285965 | 10/1988 | (EP) . |
| 0597389 | 11/1993 | (EP) . |
| 9118007 | 11/1991 | (WO) . |
| 9319366 | 9/1993 | (WO) . |
| 9508772 | 3/1995 | (WO) . |

OTHER PUBLICATIONS

Hemnilä, Clin. Chem. 31/3 359–370 (1985) "Fluoro immunoassays and Immunofluorometric Assays".*

* cited by examiner

*Primary Examiner*—Mary E. Ceperley
(74) *Attorney, Agent, or Firm*—Foley & Lardner

(57) ABSTRACT

Particles and methods for the detection or visualization of analytes using fluorescence energy transfer. Particles comprising an energy donor as a first component and a fluorescent dye as a second component positioned in said particles at an energy exchanging distance from one another, wherein the two components have a Stokes shift of greater than or equal to 50 nm, said particle having bound on its surface, a protein, polypeptide, nucleic acid, nucleotide or protein containing ligand analogue are disclosed and claimed.

57 Claims, 7 Drawing Sheets

*PHTHALOCYANINE*

*NAPHTHALOCYANINE*

*SILICON PHTHALOCYANINE*

*SILICON NAPHTHALOCYANINES*

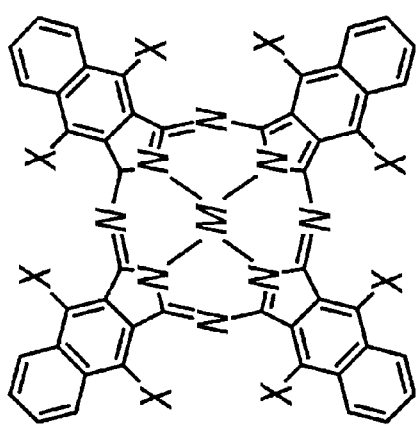
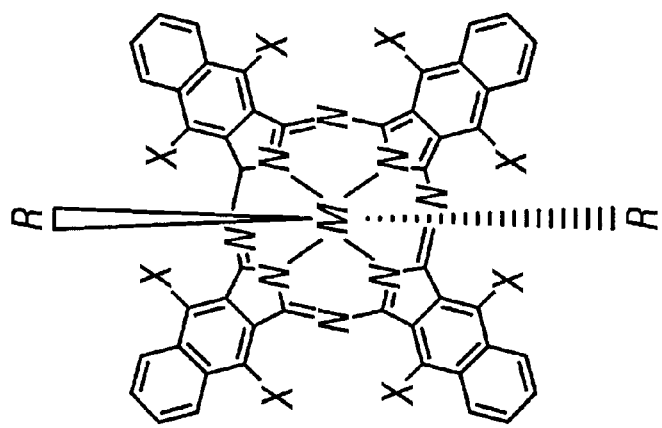
FIG. 6
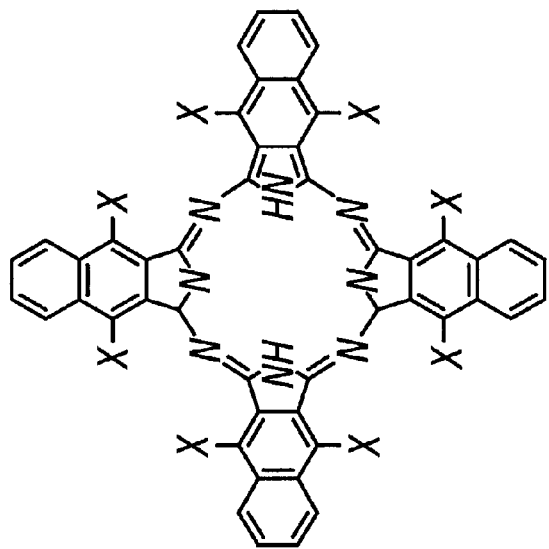

FLUORESCENCE ENERGY TRANSFER IN PARTICLES

This application is a continuation in part of application Ser. No. 08/138,708 filed Oct. 18, 1993, now abandoned, and of application Ser. No. 08/126,367 filed Sep. 24, 1993, now abandoned from which priority is claimed.

FIELD OF THE INVENTION

This invention relates generally to labels and methods for the detection or visualization of analytes and more specifically to fluorescent latex particles which incorporate fluorescence energy transfer for the detection of analytes in immunoassays.

BACKGROUND

Various methodologies are available for the visualization of cells or molecules in cells and for the measurement of analyte concentrations in fluids. Fluorescence microscopy utilizes fluorescent dyes, generally connected to specific probes, such as antibodies, for the localization of proteins and complexes in cells. For the measurement of analyte concentrations, immunoassays have become popular over the last 40 years because of the specificity of antibodies toward the analyte or target ligand. Radioimmunoassays were developed because the high specific activity of the radionuclide allowed measurement of very low concentrations of analyte. However, because of the concerns for the environment and human health, the use of radionuclides in immunoassays is becoming less popular. The use of enzymes in immunoassays to amplify a signal has been a very important advance in the field of immunoassays because their use does not involve environmental or human health hazards or risks. Enzyme-linked immunoassays, however, can be problematic because the activity of the enzyme is temperature dependent and the instability of the enzyme or the substrates can result in inaccurate quantitation of the target ligand. Still other immunoassays monitor fluorescence as the signal, with or without enzymes, for the measurement of analyte concentrations.

The characteristics of the fluorescent dyes are very important when quantifying analyte concentrations in biological fluids. For example, when the biological fluid is blood, serum or plasma, the intrinsic fluorescence of the fluid precludes the use of many dyes. These biological fluids generally have fluorescence emissions up to 600 nm when exciting at various wavelengths above 200 nm. The fluorescent signal is measured by a fluorometer which is tuned to excite the fluorescent molecule at a specific wavelength and to measure the emission of fluorescence at another wavelength. The difference in the excitation and emission wavelengths is referred to as the Stokes shift. To achieve the most sensitive measurement, the emission wavelength of the sample should not interfere with the emission of the dye. Also, the Stokes shift should be as large as possible so that the excitation light is not seen by the detector as noise. Where the Stokes shift is not large, filters or monochromators can be utilized in the fluorometer to exclude light near the emission wavelength; however, the use of filters decreases the yield of light reaching the detector and generally one circumvents this problem of light loss by the use of high intensity lamps. Thus, to avoid problems associated with small Stokes shifts and dyes which emit near the intrinsic emission of the biological fluid, a sophisticated instrument is generally built. With the advent of near-patient diagnostics in hospitals, instruments which are used for the diagnostics will become more portable and simpler to use. Therefore, there is a need for portable, simple fluorometers which can assess fluorescence in an immunoassay for the detection of analytes in biological samples.

Another problem associated with the assay of analytes in fluids or the visualization of cellular components with an intrinsic fluorescence is that of selection of the dye which is utilized as the label. The dye is generally chosen for its brightness (the product of fluorescence quantum yield and extinction coefficient) since a certain sensitivity in the assay or the visualization technique is required. However, the selection of the dye used as the label is limited when the sample has an intrinsic fluorescence because the instrument may not be capable of distinguishing sample fluorescence from dye fluorescence.

The current invention provides a methodology for the development of amplified fluorescent label systems which can be tuned to specific excitation and emission wavelengths. In addition, the methodology teaches improved methods for incorporation of dyes into particles to minimize fluorescence quenching and to maximize fluorescence intensities of the dye molecules in the particles. The novel dye systems can be utilized for the quantitation of analytes in fluids, and in particular, in biological fluids. The novel dye systems can be tuned to specific exciting and emitting wavelengths so that low current sources, such as light emitting diodes and laser diodes, and detectors, such as photo diodes, and the like, can be used in the manufacture of fluorometers which can be battery powered and portable, for use, for example, in immunoassays dedicated to near-patient diagnostics.

SUMMARY OF THE INVENTION

This invention relates to novel particles which exhibit fluorescence energy transfer (singlet-singlet energy transfer). These novel particles can be tuned to specific excitation and emission wavelengths to accommodate a wide variety of assay or visualization systems. In yet another aspect of the invention, the methodology teaches improved methods for incorporation of dyes into particles to minimize fluorescence quenching and to maximize fluorescence intensities of the dye molecules in the particles through the use of different dye molecules which possess the same or very similar excitation and emission wavelengths.

In a first aspect, the invention concerns particles that comprise an energy donor as a first component and an energy acceptor as a second component positioned in a particle at an energy exchanging distance from one another, the two components having a Stokes shift of greater than or equal to 50 nm, and the particle having bound on its surface, a protein, polypeptide, nucleic acid, nucleotide or protein containing ligand analogue. In certain embodiments, the particles also comprise at least one additional fluorescent dye as a third component that exhibits in the particle approximately the same excitation and emission wavelengths as the second component. In preferred embodiments, the particles are latex particles.

In another aspect, the invention features particles comprising an energy donor as a first component and a fluorescent dye as a second component positioned in a particle at an energy exchanging distance from one another, the two components having a Stokes shift of greater than or equal to 50 nm, and either the first or second components being phthalocyanine or naphthalocyanine. In certain embodiments, the particles also comprise at least one additional fluorescent dye as a third component that exhibits in the particle approximately the same excitation and emission wavelengths as the second component. In preferred embodiments, the particles are latex particles.

In particularly preferred embodiments, the first component is phthalocyanine and the second component is naphthalocyanine; the first component is styryl and the second component is phthalocyanine; the first component is styryl and the second component is naphthalocyanine; the first component is phenylbutadienyl and the second component is phthalocyanine; the first component is phenylbutadienyl and the second component is naphthalocyanine; the first component is phenylhexatrienyl and the second component is phthalocyanine; the first component is phenylhexatrienyl and the second component is naphthalocyanine; the first component is porphine and the second component is phthalocyanine; the first component is porphine and the second component is naphthalocyanine; the first component is a carbocyanine dye and the second component is phthalocyanine; and the first component is a carbocyanine dye and the second component is naphthalocyanine.

In other preferred embodiments, the invention relates to particles comprising an energy donor as a first component and a fluorescent dye as a second component positioned in a particle at an energy exchanging distance from one another, the two components having a Stokes shift of greater than or equal to 50 nm, the first component being a salt of trans-4-[4-(dibutylamino) styryl]-1-methyl pyridine, and the second component being silicon phthalocyanine bis(dimethylvinylsilyloxide), silicon 2,3-napthalocyanine bis(dimethylvinylsilyloxide), or a salt of 1,1-dihexyl 3,3,3,3,-tetramethylindodicarbocyanine. In certain embodiments, the particles also comprise at least one additional fluorescent dye as a third component that exhibits in the particle approximately the same excitation and emission wavelengths as the second component. In preferred embodiments, the particles are latex particles.

In further preferred embodiments, the invention features particles comprising an energy donor as a first component and a fluorescent dye as a second component positioned in a particle at an energy exchanging distance from one another, the two components having a Stokes shift of greater than or equal to 50 nm, the first component being meso-tetra-2-amninophenyl porphine, and the second component being silicon phthalocyanine bis(dimethylvinylsilyloxide), a salt of 1,1-dihexyl3,3,3',3'-tetramethylindodicarbocyanine, or silicon phthalocyanine bis(dimethylvinylsilyloxide). In certain embodiments, the particles also comprise at least one additional fluorescent dye as a third component that exhibits in the particle approximately the same excitation and emission wavelengths as the second component. In preferred embodiments, the particles are latex particles.

In other preferred embodiments, the invention relates to particles comprising an energy donor as a first component and a fluorescent dye as a second component positioned in a particle at an energy exchanging distance from one another, the two components having a Stokes shift of greater than or equal to 50 nm, the first component being a salt of 3-ethyl-3'-ethyl carboxyethyl thiacarbocyanine, a salt of 1,1'-dioctadecyl-3,3,3',3'-tetramethlyindodicarbocyanine, a salt of 1,1'-diethyl-3,3,3',3'-tetramethylindodicarbocyanine, a salt of 1,1'-dihexyl-3,3,3',3'-tetramethlyindodicarbocyanine, a salt of 3,3-diethyl thiatricarbocyanine, a salt of 3,3-dipropyl thiatricarbocyanine, a salt of 1,9-dimethylmethylene blue, a salt of N,N-di(3-trimethylammoniumpropyl)thiadicarbocyanine, a salt of 1,1',3,3 ,3',3'-hexamethylindotricarbocyanine, a salt of N-(3-triethilylammoniumpropyl)-4-(4-(p-dibutylaminophenyl) butadienyl)pyridine, a salt of 1,1',3,3,3',3'-hexamethyl-4,4'-5,5'-dibenzo-2,2' indotricarbocyanine, or chlorophyll, and the second component being silicon 2,3-napthalocyanine bis(dimethylvinylsilyloxide). In certain embodiments, the particles also comprise at least one additional fluorescent dye as a third component that exhibits in the particle approximately the same excitation and emission wavelengths as the second component. In preferred embodiments, the particles are latex particles.

In yet other preferred embodiments, the invention concerns particles comprising an energy donor as a first component and a fluorescent dye as a second component positioned in a particle at an energy exchanging distance from one another, the two components having a Stokes shift of greater than or equal to 50 nm, the first component being fluorescein or chlorophyll, and the second component being silicon phthalocyanine bis(dimethylvinylsilyloxide). In certain embodiments, the particles also comprise at least one additional fluorescent dye as a third component that exhibits in the particle approximately the same excitation and emission wavelengths as the second component. In preferred embodiments, the particles are latex particles.

DESCRIPTION OF THE DRAWING

FIG. 6 depicts naphthalocyanine derivatives which emit in the near infrared.

DETAILED DESCRIPTION

Figure 1:
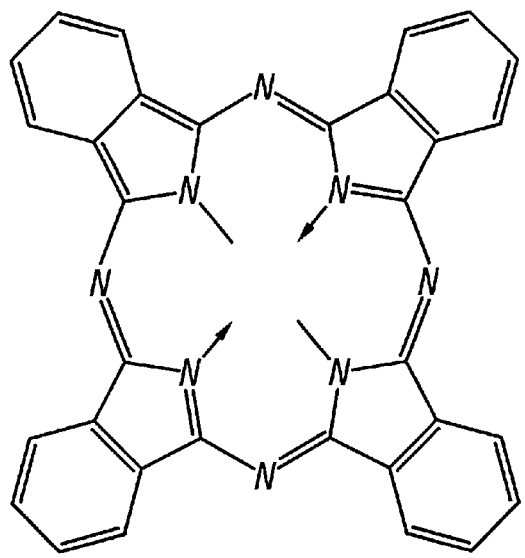
FIG. 1 depicts the structures of Phthalocyanine and naphthalocyanine.
Figure 1:
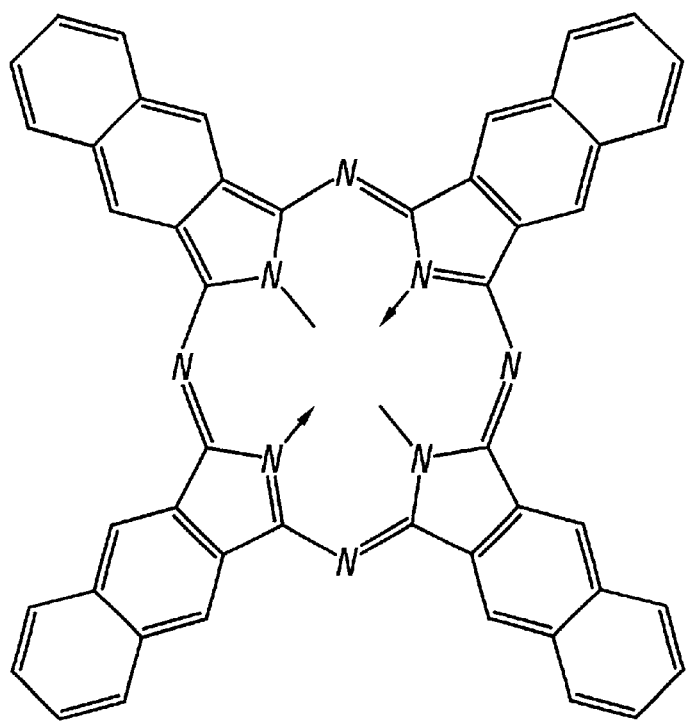

This invention describes novel particles which exhibit fluorescence energy transfer and diagnostic methods for their use. Developing a method which utilizes a fluorescent dye for the visualization of a cellular component or a cell or for an assay which quantifies an analyte in a sample requires the use of a fluorometer. The fluorescent label, the sample and the instrument must be compatible with each other to achieve an accurate measurement. Several criteria for a fluorescent label as it relates to the sample and instrument are described below. First, the absorption and emission wavelengths of the dye should not correspond to those of the specimen or sample. Second, the Stokes shift of the dye should be as large as possible to minimize the measurement of noise from the excitation wavelength. Third, the dye must be compatible with the phase of the visualization or the fluid phase of the assay; that is, the dye must be water soluble or water insoluble depending on the visualization or assay format. Fourth, the dye should be as bright as is necessary to achieve the desired sensitivity. Brightness is the product of the extinction coefficient and the quantum yield of the dye. Fifth, the instrument used to detect the fluorescent signal is generally designed around the specifications of the dye and the specimen or sample being visualized or assayed.

These points will be discussed in more detail and illustrate some of the difficulties in developing a fluorescent visualization technique or an assay using fluorescent dyes. One is limited either to dyes which have been synthesized or ones which must be synthesized in order to meet the above criteria. Those skilled in the art will appreciate that the design and synthesis of dye molecules which have a very broad range of excitation and emission wavelengths is very tedious and generally, only a very limited range of excitation and emission wavelengths can be planned for a specific molecule. The teachings of this invention allow one to prepare fluorescent labels which can be tuned to any excitation and emission wavelengths allowing for large Stokes shifts. Thus, designing a dye system with the specifications of the sample or specimen and the instrument is possible rather than designing the instrument around the specifications of the dye. Tuning the dye system to accommodate the characteristics of the sample and the instrument results in a much greater chance of success of the visualization process or the assay and greatly lowers risk.

The absorption and emission wavelengths of the dye should not correspond to those of the sample being assayed or visualized, otherwise the sample can interfere with the measurement of the fluorescent signal. When absorption or emission wavelengths of the sample do correspond to those of the dye, in practice, one dilutes, for example, a serum or blood sample so that the interference by the sample is reduced or the interfering sample is washed away from the detection area. Indeed, currently on the market, no fluorescent assay system exists for the measurement of analytes in neat biological fluids, particularly blood or serum. One reason for the lack of assay systems which measure in neat samples is that no good fluorescent dye exists which meets all the criteria listed above, particularly for measuring fluorescence in biological samples. When the sample absorbs at the excitation wavelength the amount of light which excites the sample is thus affected by the variation in the sample characteristics. For example, serum, plasma, or blood from different individuals will be different in their relative absorbtivities, which will translate into different amounts of excitation light used to excite the fluorescent label. A preferred excitation wavelength for biological fluids, including urine, blood, serum or plasma is 600 nm or greater. Particularly preferred excitation wavelengths are those which correspond to maximum light output of laser diodes and light emitting diodes. This point will be further discussed as it relates to the inventive teachings of this application.

The Stokes shift of the dye should be as large as possible to minimize the measurement of noise from the excitation source so that the signal-to-noise ratio at the limit of sensitivity is maximized. The availability of dyes with Stokes shifts greater than 100 nm is greatly limited. To further limit the usefulness of available dyes, the solubility of the dyes in aqueous samples can be a problem because most dyes with large Stokes shifts are water insoluble. The problem of a dye possessing a small Stokes shift is usually overcome in the engineering of the fluorometer by the use of monochromators or expensive optics which filter out the light from the excitation source. However, to overcome the loss in light intensity due to the filters, for example, one requires the use of high powered light sources. These light sources produce heat which must be dissipated in an instrument by using heat sinks or fans. The complexity of the fluorescence measuring device, both from an optical and a mechanical perspective, is thus greatly affected by the inadequacies of the dye system. With the advent of near-patient testing in hospitals and emergency rooms, instruments which measure fluorescence in immunoassays will be required to be portable and uncomplicated. Thus, the future state of the art for the manufacture of, for example, fluorometers which are employed for immunoassays will be required to change to simple and portable instruments. The high powered light sources and expensive optics currently incorporated into fluorometers will not meet the requirements for small, portable instruments. The inventive features of the current application teach that fluorescent labels can be prepared with large Stokes shifts and be tuned to wavelengths which are compatible with any excitation source and emission detector. The excitation and emission wavelengths of the novel fluorescent particles can be varied independently of each other.

The dye must be compatible with the fluid phase of the assay, or in other words, the dye must be water soluble or water insoluble depending on the visualization or assay format. Many fluorescent dyes are water insoluble or poorly water soluble and these dyes are not easily used for labelling molecules, proteins or cells. One skilled in the art will recognize that water insoluble dyes can be incorporated into latex particles as described in U.S. Pat. Nos. 4,326,008, 4,609,689 and 5,154,887, which are hereby incorporated by reference. Thus, water insoluble dyes can be made useful by incorporation into latex particles for visualization in a variety of assay formats.

The dye should be as bright as is necessary to achieve the desired sensitivity. If one knows the extinction coefficient and the quantum yield of the dye and the concentration of the target to be measured, it can be estimated whether the dye is bright enough to achieve the desired sensitivity. Incorporation of dyes into latex particles or the utilization of an enzyme which catalyzes the production of a fluorescent substrate are examples of techniques which one skilled in the art uses as amplification systems.

The instrument used to detect the fluorescent signal is generally designed around the specifications of the dye and the specimen or sample being visualized or assayed because of the limited numbers of dyes which can be successfully used. As discussed above, the components of the instrument are selected for a particular dye system since a successful instrument must be highly tuned to eliminate background noise from the excitation source.

Each of the conditions described above, taken together, greatly narrows the development of dye systems which can be employed for measuring sub-picomolar concentrations of analytes, particularly in biological fluids. The limitations also impose restrictions on the design of an instrument to measure the fluorescence. The novel teachings of this application allow the design and tuning of dye systems to match any instrument design. The concept is to either incorporate or adsorb at least two dyes into or onto particles, which, as a pair, exhibit fluorescence energy transfer. The particles which can be used are those which absorb dyes on the surface or inside the particle or those which have dyes covalently attached, and include latex particles, silica, alumina, various colloids and the like. The selection of the dye pairs is based on their ability to exhibit energy transfer at the appropriate excitation wavelength of the donor dye and the emission of the acceptor. Fluorescence energy transfer of two molecules is well known to those skilled in the art and the rate of energy transfer was described by F örster (Ann. Physik. (1948) 2,55–75). Fluorescence energy transfer has been used as a spectroscopic ruler to predict proximity relationships in proteins, RNA and peptides (Annual Review of Biochemistry (1978), 47, 819–846) and also to probe geometrical details in particles (Physical Review Letters (1988) 61, 641–644). U.S. Pat. Nos. 4,542,104 and 4,666,862 describe fluorescence energy transfer in phycobiliproteins. These dye complexes are described for use as labels in immunoassays, however, the limited use of phycobiliproteins and the expense of these natural protein complexes make them undesirable for use on a commercial scale.

The novel fluorescent particles of this invention are composed of at least two dyes which are positioned in the interior or on the exterior of particles at an energy exchanging distance. One skilled in the art will recognize that various particles can be utilized, such as latex, silica, alumina and various colloids. Particularly preferred particles are latex particles. The selection of the dye molecules for incorporation into the particles should be related to the specific use of the particles and the instrument for measuring the fluorescence. For example, when developing an assay for an analyte in a biological medium, such as serum, the intrinsic absorbance and fluorescence of the serum must be considered. Serum absorbs in the ultraviolet spectrum as well as in the visible spectrum up to around 500 nm and the intrinsic fluorescence of serum broadly approaches 600 nm. The ideal dye couple would include the donor dye which would absorb at above 500 nm and emit at a wavelength which the acceptor dye absorbs, and the acceptor dye should emit at a wavelength above 600 nm. The serum then does not affect fluorescence of the acceptor dye because the serum poorly absorbs at the absorption of the donor dye and the acceptor dye emits at a wavelength where the serum does not fluoresce.

Fluorescent dye molecules incorporated into or onto particles will exhibit fluorescence quenching because of the close proximity of the dyes to each other and to the matrix of the particle. The dyes are positioned in the particle at an energy exchanging distance from one another which allows singlet-singlet energy transfer. When loading dyes into or onto particles, one must optimize the concentration of dye as it relates to quenching. The dyes can be loaded successively or together. The degree of quenching can be quantified by measuring the fluorescence emission of a dilute suspension of particles (about 0.001% to 0.1% solids) in water and then also measuring the fluorescence of the same concentration of particles in solvent which liberates the dyes from the particle. The ratio of the fluorescence intensities (fluorescence intensity of incorporated dyes divided by the intensity of liberated dyes minus 1) is the amount of quenching of the dyes in the particle. In practice, one incorporates dyes at various concentrations and measures the fluorescence intensities of the incorporated and liberated dyes to optimize the intensity of fluorescence of the particle while minimizing the quenching of fluorescence in the particle.

The inventive teachings described herein provide for particles with reduced quenching and improved fluorescence intensities. A large majority of fluorescent molecules are aromatic, that is, they possess 4n+2 pi electrons. The resultant aromatic character promotes stacking of the molecules, especially of water insoluble molecules in aqueous solutions or in particles, which in turn promotes fluorescence quenching. The novel fluorescent particles described in this application are incorporated with dyes which, through steric interference of the dye molecules, their propensity to stack in the particles is minimized. In another aspect of this invention, fluorescence quenching of dye molecules in particles is minimized by employing different dyes with approximately the same excitation and emission wavelengths. That is, the wavelength maximum for excitation and emission of the different dyes are within about 10 nm of each other so that there is substantial overlap of the peaks. One skilled in the art can appreciate that the width of excitation and emission spectra of various dyes can vary. The principle here is that different dyes will not stack in an organized orientation with each other to the same degree as dyes which are the same. An analogy to this stacking principle is the depression of the melting point of a pure compound by an impurity. It is well known to physical chemists that an impurity in a solid compound lowers its melting point because the impurity disrupts the formation of the crystal lattice of the pure compound. Incorporating dyes into or onto particles using organic solvents and then removing the solvent causes the dye to precipitate or crystallize in the particle. The disruption of the crystalline lattice of dye molecules in particles will alter the stacking of the molecules and thereby reduce quenching. Thus, incorporation of dissimilar dye molecules with similar excitation and emission spectra improves fluorescence intensities of the particles by decreasing the quenching interactions of the molecules.

In another aspect of this invention, incorporation into particles of dissimilar dyes which exhibit fluorescence energy transfer in the particles will also disrupt the others crystalline lattice formation. Thus, the fluorescence intensities of particles exhibiting fluorescence energy transfer will be improved as a result of decreasing quenching in the particle because the stacking of similar dyes in the particles is disrupted by the other dye.

One skilled in the art can appreciate that more than one dye pair which exhibits fluorescence energy transfer can be incorporated into or onto particles resulting in a class of particles which fluoresce at different wavelengths. In addition, with the inventive teachings described herein, incorporation into or onto particles of 3 or more dyes, which together provide a cascade of energy transfer from the absorber to the intermediate donor to the acceptor (which fluoresces), can result in the production of particles with very long Stokes shifts and allows one to produce particles with nearly an unlimited variety of excitation and emission characteristics.

Figure 2:
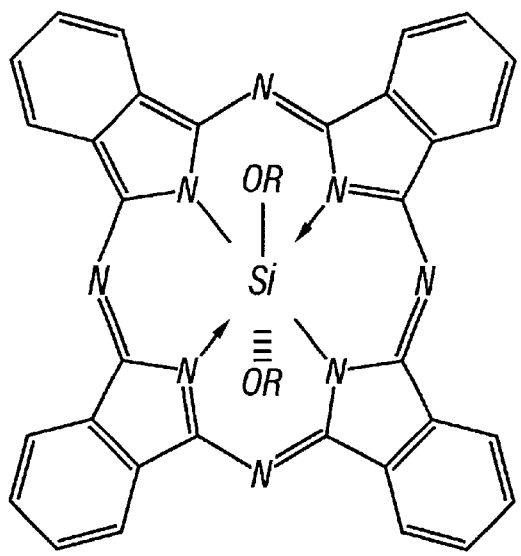
FIG. 2 depicts the structures of Silicon phthalocyanine and Silicon Naphthalocyanine.
Figure 2:
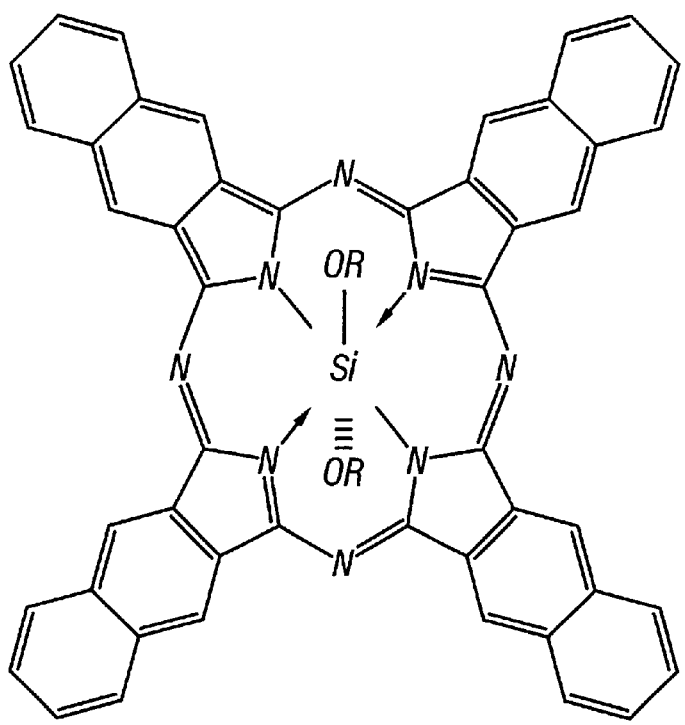
Figure 3A:
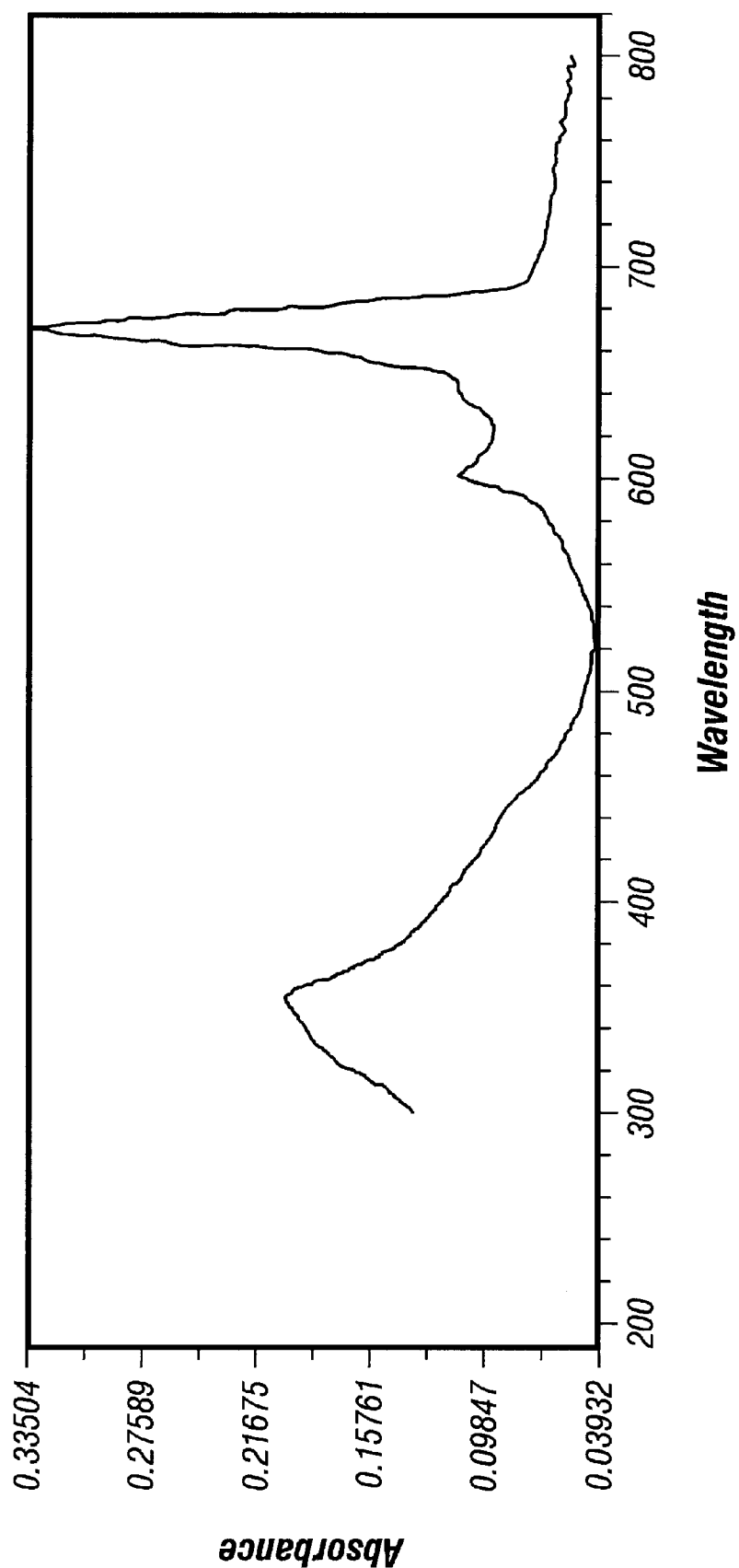
FIG. 3 depicts the spectra of Silicon Phthalocyanine dihydroxide and the spectra of Silicon 2,3 Naphthalocyanine dihydroxide.
Figure 3B:
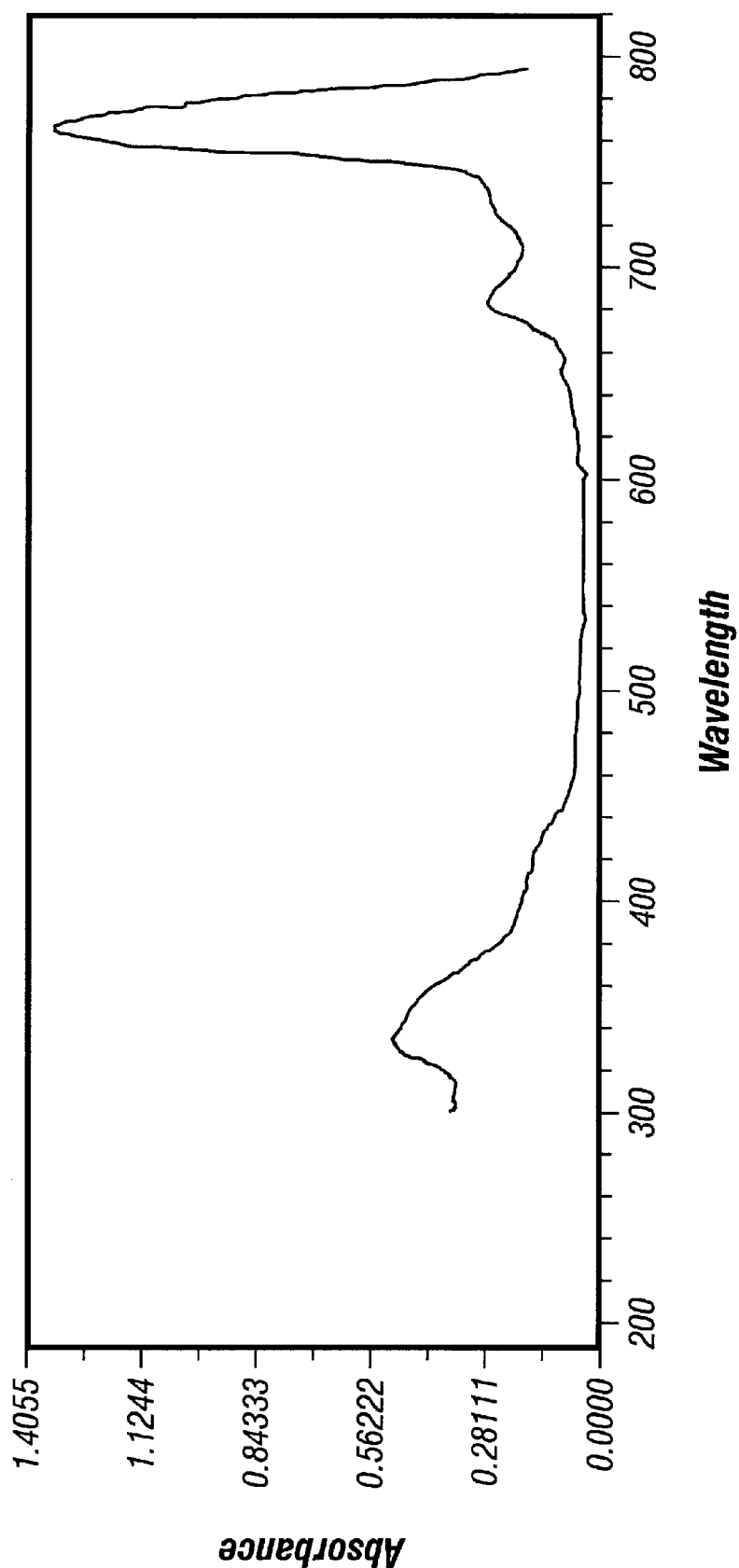

FIG. 1 shows preferred acceptor dyes which are phthalocyanines and naphthalocyanines. FIG. 2 shows particularly preferred acceptor dyes which are derivatives of silicon phthalocyanines and naphthalocyanines, where R is hydrogen or an alkylcarbon chain from 1–20 carbons, either saturated or unsaturated, having 0–10 heteroatoms (N,O,S), and having 0 or 1 silox-ide groups. The best mode compounds are those in which R=
$Si(CH_3)_2C_6F_5$
$Si(C_6H_{13})_3$
$Si(CH_3)_2(CH_2)_3CN$
$Si(CH_3)_2(CH_2)_{10}COOCH_3$
$Si(CH_3)_2CH=CH_2$
$Si(CH_3)_2(CH_2)_{10}COOH$
$Si(CH_3)_2(CH_2)_4Cl$; and
$Si(CH3)_2(CH_2)_6CH=CH_2$.
The parent compounds of phthalocyanines and naphthalocyanines are preferred because their emission wavelengths are around 680 nm and 780 nm in latex particles, respectively, and their quantum yields approach 70%. These emission wavelengths are particularly useful for quantifying fluorescence in biological samples. Those skilled in the art can appreciate that derivatives of the phthalocyanines and naphthalocyanines can be synthesized, for example, derivitization of the phenyl or naphthyl rings with various substitutes, respectively, to yield different molecules but these variants, also are within the scope of this application. The choice of the donor dye to excite the phthalocyanine or naphthalocyanine dyes is dependent on having a donor dye emission wavelength which corresponds to the appropriate range of absorbance wavelengths of the phthalocyanines or naphthalocyanines. FIG. 3 shows the absorbance spectra of the silicon dihydroxyphthalocyanine and silicon dihydroxynaphthalocyanine in dimethylformamide. A potential range of excitation of the these acceptor dyes by the donor dye is between approximately 550 nm and 670 nm and 600 nm and 760 nm, respectively. One skilled in the art will recognize that many dyes would be candidates for the donor dye because of the wide useful range of wavelengths which can excite the acceptor dyes. The choice of the acceptor dye should meet the criteria outlined above. Several examples are described which illustrate the versatility of this novel approach. Assume that an instrument is to be built with an excitation source which has a maximum intensity at 480 nm and a detector which has a good quantum efficiency at 600 to 700 nm. The donor dye should thus be capable of being excited at 480 nm and further assuming that a phthalocyanine derivative is the acceptor dye for emission at 680 nm, then the donor should emit in the range of 550 to 670 nm.

Preferred classes of dyes for this application are styryl, phenylbutadienyl and phenylhexatrienyl dyes. Styryl dyes are those of the following formula:

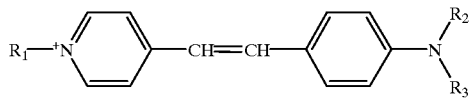

and phenylbutadienyl dyes are of the formula:

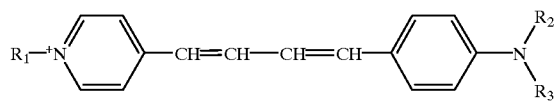

and phenylhexatrienyl dyes are of the formula:

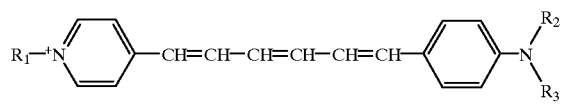

wherein R1, R2 and R3 can be the same or different and R1, R2 and R3 are H or alkylcarbon chains from 1–20 carbons, either saturated or unsaturated, and having 0–10 heteroatoms (N, O, S).

In general, these dye classes excite approximately between about 470 and 530 nm and emit approximately between 600 and 780 nm (see Molecular Probes Handbook of Fluorescent Probes and Research Chemicals by Richard P. Haugland, 1992–1994, p. 156). A particularly preferred styryl dye is the trans-4-[4-(dibutylamino)styryl]-1-methylpyridinium iodide (Aldrich Chemical Co.) which has its maximum absorbance at 486 nm in dimethylformamide and its emission is at 600 nm. One skilled in the art will recognize that the substituents of f the aniline nitrogen and the pyridium nitrogen of these classes of dyes can vary and that preferred substituents are those with hydrophobic groups to maintain water insolubility. In another application of this novel technology, an instrument system is built which has a source of maximum intensity at 420 nm and a detector as described in the above example. The dye system here can include the phthalocyanine acceptor; however, a different donor must be employed. A preferred donor for this application is a meso-tetra-2-aminophenylporphine (Porphyrine Products, Inc., Logan Utah) which has a maximum absorbance at 418 nm in dimethylsulfoxide and an emission around 655 nm. This porphyrin will excite the phthalocyanine derivative in latex particles and the dye system will emit at 680 nm. In yet another application, an instrument system is built to perform immunoassays in serum or in various biological specimens and the excitation source is around 650 nm to avoid interference by the serum sample. The detector has good quantum efficiency at 700 to 800 nm so a preferred acceptor dye is a naphthalocyanine derivative which has an emission at approximately 780 nm, an emission wavelength which is generally not in common with serum samples or biological specimens. A donor dye for the naphthalocyanine acceptor should absorb at around 650 nm to coincide with the source and emit between approximately 660 nm and 760 nm. Preferred classes of dyes for this donor application are the carbocyanine dyes and the ethenyl-substituted dipyrromethencboron di fluoro dyes, as described in U.S. Pat. Nos. 5,187,288, 5,248,782 and 5,274,113.

Carbocyanine dyes, which generally excite between 500 and 750 nm (see Molecular Probes Handbook) are of the general formula:

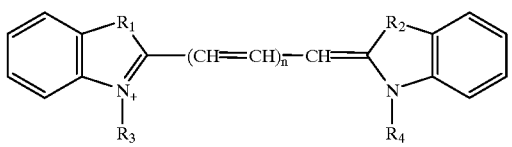

wherein N is 1 or 2; or 3; wherein R1 and R2 are S, N, or O; and wherein R3 and R4 are H or alkylcarbon chains of from 1–20 carbons, either saturated or unsaturated and having 0–10 heteroatoms (N, O, S).

Carbocyanine dyes also are of the general formula:

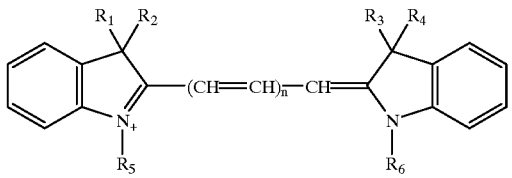

wherein N is 1 or 2; or 3; wherein R1–R6 are H or alkylcarbon chains of from 1–20 carbons, either saturated or unsaturated and having 0–10 heteroatoms (N, O, S).

Figure 4:
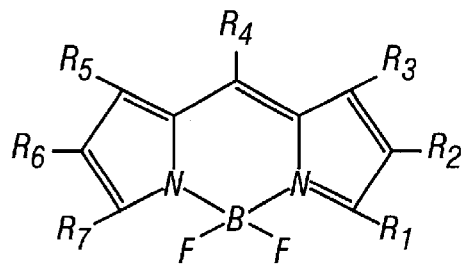
FIG. 4 depicts the general structure of ethenyl-substituted dipyrromethenboron difluoro dyes.

Ethenyl-substituted dipyrromethencboron difluro dyes, which generally excite above 500 nm (see Molecular Probes Handbook) are of the general formula as depicted in FIG. 4, wherein R1–R7 include substituents as described in U.S. Pat. Nos. 5,187,288, 5,248,782 and 5,274,113.

Particularly preferred donor dyes are 1,1'-dihexyl-3,3,3', 3'-tetramethylindocarbocyanine iodide, 1,1'-diethyl-3,3,3', 3',-tetramethylindodicarbocyanine iodide and (E,E)-3,5-bis-(4-phenyl-1,3-butadienyl)-4,4-difluoro-4-bora-3a,4a-diazo-5-indacene (from Molecular Probes Inc., Eugene, Oreg.) which have absorption maximums of 642 nm, and 645 nm and 650 nm and emission maximums of 674 nm and 665 nm, and 670 nm, respectively, in dimethylformamide. Particles incorporated with these particularly preferred dyes and a naphthalocyanine derivative will excite with the 650 nm source and emit at approximately 780 nm. One skilled in the art will recognize that the excitation and emission spectra for any particular dye has a Gaussian form and therefore the excitation source does not need to correspond exactly to the excitation maximum of the donor dye in order to obtain an intense fluorescent signal. Likewise, the donor emission does not have to coincide with the highest absorption of the acceptor dye in order to achieve efficient energy transfer. One skilled in the art will also recognize that the substituents at and on the 1 and 3 positions of the carbocyanines and the substituents at the R1 and R7 positions of the dipyrromethaneboron difluoro dyes, and the conjugation between the ring structures can vary and these variations are also useful in tuning fluorescence spectra of the particles.

Figure 5:
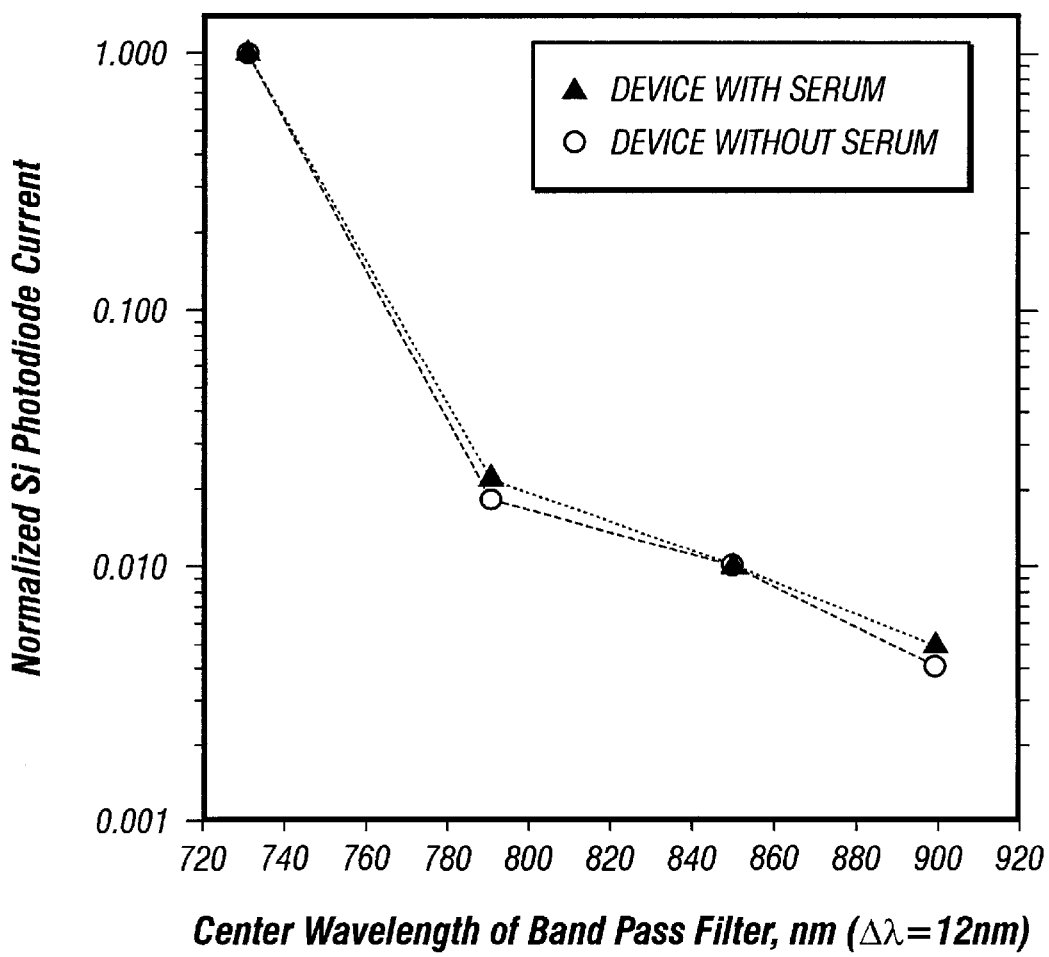
FIG. 5 depicts the attenuation of the background signal as a function of increasing wavelength. The data was measured using a device as described in Applicant's allowed Ser. No. 07/887,526 filed May 21, 1992, now U.S. Pat. No. 5,458,852, entitled "Diagnostic Devices and Apparatus for the Controlled Movements of Reagents Without Membranes," which is hereby fully incorporated herein.

Also preferred emission wavelengths of the particles range from about 800 nm to 1000 nm. This near infra-red is important because the scattering component of the light decreases substantially, thus lowering the background of the fluorescent measurement. For example, FIG. 5 illustrates the attenuation of the background signal as the wavelength of the measured light increases from 730 nm to 900 nm in an immunoassay device, as described in allowed application Ser. No. 07/887,526 (which is herein incorporated by reference), now U.S. Pat. No. 5,458,852, containing either neat human serum or no serum. This figure shows that the background decreases by a factor of 5 when measuring at 900 nm as compared to 790 nm when the illumination source is a 1 milli watt ("mW") 670 nm laser diode. In addition, excitation of neat serum at 670 nm does not result in a significant measurable fluorescence between 730 nm and 900 nm. Thus, for example, the signal to noise ratio of the measurement of fluorescence emission of a dye which emits at around 900 nm as compared to a dye emitting at around 790 nm would be improved by a factor of 5. Maximizing the signal to noise ratio, in general, is commonly sought in analytical chemistry because the sensitivity of the measurement is improved. Preferred dyes, for example as described in J. Chem. Soc. Perkin Trans. 1, (1988), 2453–2458, which emit above 780 nm include derivatives of the naphthalocyanine class (FIG. 1) and are characterized by the general formulae, as depicted in FIG. 6, where M is a metal such as Si, Ge, Al, Sn and Ti and the like, and where R is an alkyl or aryl, and wheree X is an electron donating group or groups which can be the same or different, including, but not limited to aryl and —OZ, where Z is alkyl or aryl. The electron donating character of the X group or groups redshifts the emission wavelength as compared to the general naphthalocyanine compounds (FIG. 1). For example, the compounds described in examples 26, 27 and 28 are illustrative of dyes which have emission wavelengths around 850 nm. These preferred dyes would yield an improved signal to noise ratio as compared to dyes emitting at 780 nm (See FIG. 5). Preferred donor dyes for this class of near infra-red emitting dyes are those which have emission wavelengths which correlate to the absorbance characteristics of the acceptor dye. Preferred dyes for this application are the ethenyl-substituted dipyrromethaneboron difluoride dyes, as described in U.S. Pat. Nos. 5,187,288, 5,248,782 and 5,274, 113.

Figure 7:
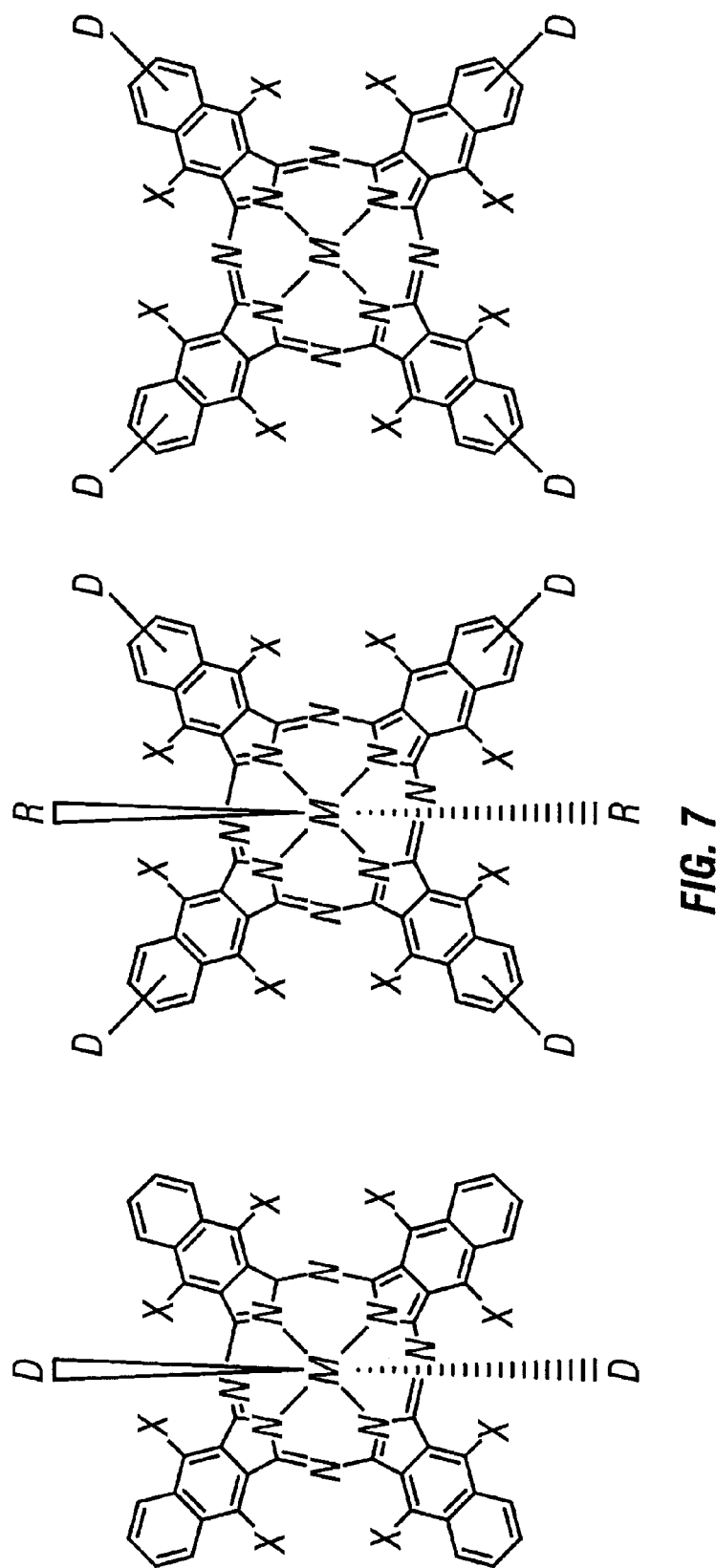
FIG. 7 depicts general structures of fluorescent energy transfer naphthalocyanine compounds.

The geometrical orientation of the donor dye to the acceptor dye will affect the efficiency of energy transfer between the donor and acceptor dyes. Thus, the donor and acceptor dyes can be synthesized to form an optimal compound, which, in solution, exhibits fluorescence energy transfer ("FET") in an efficient manner. The optimized FET compound then may be incorporated into particles. Preferred naphthalocyanine copounds are those as depicted in FIG. 7, where X is hydrogen or electron donating groups, such as —OZ, where Z is alkyl or aryl and D is the donor dye covalently attached to the naphthalocyanine derivative at a distance which allows for energy transfer between the donor and acceptor. Generally, the distances between donor and acceptor are about 5 angstroms to 30 angstroms, and preferably from 5 angstroms to 15 angstroms. In addition, each naphthalocyanine derivative can have 1–4 donor dyes attached, depending on the required application of FET compound. Suitable donor dyes are those which emit in the absorbance range of the acceptor dye. Example 29 describes the synthesis of a fluorescein-silicon phthalocyanine FET compound. Example 30, item numbered 88, shows the fluorescence characteristics of this compound in latex particles. One skilled in the art will appreciate that with the inventive teachings described herein, that many FET compounds may be synthesized for any particular application of excitation and emission.

Another approach to developing particles which exhibit fluorescence energy transfer is to synthesize unsymmetrical phthalocyanines or naphthalocyanines, as described, for example, in J. Am. Chem. Soc. (1990), 112, 9640–9641, and references described therein. These unsymmetrical phthalocyanines and naphthalocyanines can be synthesized to optimize the excitation and emission wavelengths. The resulting compound is then incorporated into particles to yield particles which have excitation wavelengths above 600 nm and emission wavelengths above 680 nm.

Preferred molar ratios of donor to acceptor dyes in the latex particles generally range from about 20:1 to about 1:20 and particularly from about 1:1 to 6:1. The desired fluorescence intensity should be obtained through experimentation by incorporating various ratios of donor to acceptor dyes into the particles at various dye concentrations.

Preferred particle sizes range from about 0.1 nm to 5000 nm and preferably from about 1 nm to 1000 nm. The choice of particle size should be related to the specific function for the label. The particle size may vary for a particular application. For example, in an immunoassay, if the label requires a more intense fluorescence for measuring very low concentrations of analytes then one would employ larger particles because larger particles can incorporate more dye molecules. The small particle sizes (0.1–1 nm) may be employed in fluorescence polarization assays, as described for example, in U.S. Pat. Nos. 4,420,568, 4,476229 and 4,510,251, in in vitro visualization of cellular components or in in vivo imaging techniques.

The resulting fluorescent dye particles which exhibit the appropriate excitation and emission characteristics are further adsorbed or chemically reacted with various nucleic acids, nucleotides, proteins or peptides and the like which are required for a specific purpose. The adsorption of macromolecules to particles, particularly latex particles is well known to those skilled in the art and generally involves adsorption of the macromolecule at a temperature between 5° C. and 50° C. and at a pH which is below the pI of the molecule. For example, fluorescent particles exhibiting fluorescence energy transfer can be adsorbed with either antibodies for use in non-competitive immunoassays or ligand analogues for use in competitive immunoassays in reaction mixtures of the assays. In the case of non-competitive assays, the reaction mixture would include at least one target ligand and at least one class of fluorescent particles having bound thereto at least one receptor specific for target ligand, forming an antibody (fluorescent) conjugate. In the case of competitive assays, the reaction mixture will include at least one target ligand, at least one receptor specific to the target ligand, and at least one class of fluorescent particles, having bound thereto at least one ligand analogue, forming a ligand analogue (fluorescent) conjugate. The antibody conjugates bound to target ligands in the non-competitive reaction mixture and the ligand analogue conjugates not bound by receptors specific to the target ligands in the competitive reaction mixture can be bound to a solid phase consisting of receptors specific to another epitope of the target ligand of the target ligand-antibody conjugate complexes and of receptors specific to ligand analogues of the ligand analogue conjugates, respectively. The fluorescent conjugates unbound by the solid phase are removed and the fluorescence of the bound conjugates is measured. The measured fluorescence is related to the target ligand concentration. The various reagents described above can also be attached covalently to the latex particles. For example, antibodies or ligand analogues can be attached through amine or carboxylic acids to carboxylic acids or amines on the surface of the particles, respectively, to form stable amide linkages. Those skilled in the art will appreciate that the novel fluorescent particles described herein have many uses in immunoassays, fluorescence microscopy, in vivo imaging, in vitro cancer therapy and cell sorters and the like.

EXPERIMENTAL SECTION

Fluorescence measurements were performed on a Perkin-Elmer model LS 50B Luminescence Spectrometer for dyes emitting around 780 nm. In some instances, dyes emitting above 800 nm were measured according to Example 18. Absorbance measurements were performed on a Hewlett Packard 8452A Diode Array Spectrophotometer.

EXAMPLE 1
Synthesis of Silicon Phthalocyanine Dihydroxide SiPc $(OH)_2$

A suspension of silicon phthalocyanine dichloride (1.83 g, 3.0 mmol) in pyridine (50 mL) and water (50 mL) was refluxed with stirring on an oil bath at 120° C. for 18 h. After cooling the dark blue solid product was filtered and the residue was washed with water (10 mL), acetone (5 mL) and then dried under vacuum to afford 1.71 g of the title compound.

EXAMPLE 2
Synthesis of Silicon Phthalocyanine bis(trihexylsilyloxide) (PcSi trihexyl)

A suspension of silicon phthalocyanine dihydroxide (115 mg, 0.2 mmol) in anhydrous pyridine (11 mL) containing chlorotrihexylsilane (733 uL, 2.0 mmol) was refluxed on an oil bath at 130° C. for 5 h. The resulting purple solution was allowed to cool and was evaporated. The resulting slurry was treated with ice-cold hexane (2 mL) and the dark blue solid product was filtered, washed with ice-cold hexane (2 mL) and was dried under vacuum to yield 249 mg of crude product. The crude product in chloroform was purified on an Alumina column (Activity 1) equilibrated in hexane and the product was eluted with hexane/toluene (2/1, v/v) as a bright blue band. The solvent containing the product was evaporated to yield 69 mg of the title compound with a mp 171° C. (lit mp 175° C.).

EXAMPLE 3
Synthesis of Silicon Phthalocyanine Bis[(10-carbomethoxydecyl)dimethyl Silyloxide] (PcSi Methyl Ester)

To a suspension of silicon phthalocyanine dihydroxide (115 mg, 0.2 mmol) in anhydrous pyridine (11 mL) was added (10-carbomethoxydecyl)dimethylchlorosilane (586 mg, 2 mmol) and the mixture was refluxed with stirring on an oil bath at 130° C. for 5 h. The dark blue solution was allowed to cool and the solvents were evaporated. The residue was purified on a Silica gel 60 column equilibrated in hexane and the product eluted slowly as a blue band with toluene. The toluene fraction containing product was evaporated, hexane (10 ml) was added to the residue and the blue product was filtered, washed with hexane and dried to afford 105 mg of the title compound.

EXAMPLE 4
Synthesis of Silicon Phthalocyanine Bis (dimethylvinylsilyloxide) (PcSi Vinyl)

To a suspension of silicon phthalocyanine dihydroxide (115 mg, 0.2 mmol) in anhydrous pyridine (11 mL) was added chlorodimethylvinylsilane (276 uL, 20 mmol) and the mixture was refluxed with stirring on an oil bath at 130° C. for 5 h. The dark solution was allowed to cool and was evaporated. The residue was purified on a Silica gel 60 column equilibrated in hexane and the product was eluted with toluene as a blue band. The eluate containing product was evaporated, the residue treated with hexane and the dark blue solid product was filtered, washed with hexane and was dried under vacuum to afford 7.5 mg of the title compound.

EXAMPLE 5
Synthesis of Silicon Phthalocyanine Bis[(3-cyanopropyl)dimethylsilyloxide] (PcSi Cyano)

To a suspension of silicon phthalocyanine dihydroxide (115 mg, 0.2 mmol) in anhydrous pyridine (11 mL) was added chloro(3-cyanopropyl)-dimethylsilane (328 uL, 20 mmol) and the mixture was refluxed with stirring on an oil bath at 130° C. for 5 h. The purple solution was allowed to cool and was evaporated. The residue was purified on a Silica gel 60 column equilibrated in hexane. The column was washed with toluene and the product was eluted with toluene/isopropyl alcohol (90/10, v/v) as a bright blue band. The eluate containing product was evaporated under vacuum to afford 101 mg of the title compound with a mp>260° C.

EXAMPLE 6
Synthesis of Silicon Phthalocyanine Bis (dimethylpentafluorophenylsilyloxide) (PcSi Pentafluoro)

To a suspension of silicon phthalocyanine dihydroxide (115 mg, 0.2 mmol) in anhydrous pyridine (11 mL) was added chlorodimethylpentafluorophenylsilane (376 uL, 20 mmol) and the mixture was refluxed with stirring on an oil bath at 130° C. for 5 h. The dark green solution was allowed to cool and was evaporated. The residue was purified on a Silica gel 60 column equilibrated in hexane. The product was eluted with toluene as a dark blue band. The eluate containing the product was evaporated, the residue was treated with hexane (10 mL) and the dark blue solid product was filtered, washed with hexane and was dried under vacuum to afford 73 mg of the title compound.

EXAMPLE 7
Synthesis of Silicon 2,3-Naphthalocyanine Dihydroxide (NaPcSi Hydroxide)

A suspension of silicon 2,3-naphthalocyanine dichloride (280 mg, 0.34 mmol) in pyridine (10 ml) and water (10 ml) was refluxed with stirring on an oil bath at 130° C. for 24 h. After cooling to room temperature, the dark green solid product was filtered and, the residue was washed, successively, with water (5 ml) and acetone (2 ml). The product was dried under vacuum to afford 217 mg of the title compound.

EXAMPLE 8
Synthesis of Silicon 2,3-Naphthalocyanine Bis (dimethylvinylsilyloxide) (NaPcSi Vinyl)

To a suspension of silicon 2,3-naphthalocyanine dihydroxide (87 mg, 0.11 mmol) in anhydrous dimethylformamide (1 ml) was added chlorodimethylvinylsilane (0.042 ml, 0.3 mmol), followed by imidazole (14 mg, 0.2 mmol). The mixture was stirred under argon at room temperature for 24 h. The solvents were evaporated and the residue was purified on a Silica gel 60 column which was equilibrated in hexane. The product was eluted with toluene as a green band. The toluene fraction containing the product was evaporated and the residue was treated with hexane. The dark green solid was filtered, washed with hexane and was dried under vacuum to afford 26 mg of the title compound.

EXAMPLE 9
Synthesis of Silicon 2,3-Naphthalocyanine Bis (dimethylpentafluorophenylsilyloxide (NaPcSi Pentafluoro)

To a suspension of silicon 2,3-napthalocyanine dihydroxide (87 mg, 0.11 mmol) in anhydrous pyridine (5 ml) was added chlorodimethylpentafluorophenylsilane (0.188 ml, 1 mmol). The mixture was refluxed with stirring on an oil bath at 130° C. for 5 h. After cooling, the solvent was evaporated and the residue was purified on a Silica gel 60 column which was equilibrated in hexane. The product was eluted with toluene as a green band. The toluene fraction containing the product was evaporated and the residue was treated with hexane. The dark green solid was filtered, washed with hexane and was dried under vacuum to afford 23 mg of the title compound.

EXAMPLE 10
General Procedures for the Preparation of Dye-loaded Latex Particles of Varying Sizes The various dyes were loaded into latex particles of varying sizes according to the general procedures outlined below. Two procedures are described and involve swelling latex particles with aqueous solutions of either tetrahydrofuran or dimethylformamide prior to addition of the dye solutions. Latex particle sizes used range from 67 nm to 783 nm and one skilled in the art recognizes that smaller and larger particles can be used. The choice of the organic solvent used to swell the particles depends solely on the solubility of the various dyes in either solvent. Tables 1 and 2 of Example 15 below show the aqueous organic solvent system and the optimum dye concentration which were used for the loading into particles for each dye pair of a selected number of dyes. One skilled in the art recognizes that many changes can be made to these procedures to prepare particles with different degrees of fluorescence intensities and quenching by loading higher or lower amounts of dye in the particles and also by changing the ratios of each dye pair to the other. One skilled in the art also recognizes that similar techniques are useful for incorporation of dyes into latex particles, for example, as described in U.S. Pat. Nos. 4,199,363 and 4,368,258.

Surfactant-free polystyrene sulfate latex particles in sizes ranging from 67 nm to 783 nm and caroxyl-modified latex ("CML") particles ranging from 200 nm to 400 nm particles were obtained through Interfacial Dynamics Corp. Inc., Portland Oreg.

Method 1 Utilizing Tetrahydrofuran

Tetrahydrofuran (0.36 ml) was added, dropwise over a 5 min period, to a stirring solution of 1.6 ml of 2.5% solids of latex particles at room temperature. The latex suspension was stirred at room temperature for an additional 30 min to swell the latex. The dye solution (0.04 ml), which consists of one or both dyes at an appropriate concentration in tetrahydrofuran, was added dropwise over 5 min to the stirred latex solution, to give the loading dye concentration (in 2 ml volume) as indicated in Table 1. The latex-dye solution was stirred at room temperature for 30 min in the dark. The latex solution was then transferred to dialysis tubing (Spectra-por, 12–14,000 molecular weight cutoff, Spectrum, Houston, Tex.) and the dye-latex solutions were dialyzed against water for 12 to 15 hours at 4° C. The dye-latex solutions were removed from dialysis and the % solids of the solutions was calculated from the final volume after dialysis and the starting solids concentration.

Method 2 Utilizing Dimethylformamide

Dimethylformamide (1.33 ml) was added, dropwise over a 5 min period, to a stirring solution of 0.6 ml of 6.7% solids of latex particles at room temperature. The latex suspension was stirred at room temperature for an additional 30 min to swell the latex. The dye solution (0.07 ml), which consists of one or both dyes at an appropriate concentration in dimethylformamide, was added dropwise over 5 min to the stirred latex solution, to give the loading dye concentration (in 2 ml volume) as indicated in Table 1. The latex-dye solution was stirred at room temperature for 30 min in the dark. The latex solution was then transferred to dialysis tubing (Spectra-por, 12–14,000 molecular weight cutoff, Spectrum, Houston Tex.) and the dye-latex solutions were dialyzed against water for 12 to 15 hours at 4° C. The dye-latex solutions were removed from dialysis and the t solids of the solutions was calculated from the final volume after dialysis and the starting solids concentration.

EXAMPLE 11
Effect of Varying Dye Loading Concentration on Fluorescence Intensity and Optimization of Fluorescence Intensity Latex Particles The incorporation of dye into latex particles must be optimized in order to achieve the maximum fluorescence intensity and to minimize the degree of fluorescence quenching of the dye molecules. Fluorescence quenching can be significant because of the close proximity of the dye molecules in the particles. The PcSi vinyl was incorporated into 67 nm latex particles (polystyrene sulfate from Interfacial Dynamics Corp., Inc., Portland, Oreg.) using method 1 (example 10) at various concentrations as indicated in the table below. The dye latex particles were diluted to 0.0019% solids in either water or tetrahydrofuran for each dye concentration. The solutions were excited at 350 nm and the emission at 680 nm was measured. The fluorescence intensity in water divided by the intensity in tetrahydrofuran minus 1 times 100 is the % quenching in the particles. The table below shows the fluorescence intensities as a function of dye loading concentrations and quenching for each condition.

| Loading Dye Concentration (mg/ml) | Intensity (680 nm) | Quenching (%) |
|---|---|---|
| 0.01 | 420 | 41 |
| 0.025 | 489 | 65 |
| 0.05 | 492 | 73 |
| 0.075 | 401 | 76 |
| 0.1 | 338 | 83 |
| 0.15 | 197 | 87 |
| 0.3 | 91 | 90 |
| 0.9 | 34 | 96 |

These results show that an optimum loading dye concentration gives the highest fluorescence intensities and the lowest quenching. In this case, a dye concentration of between 0.025 and 0.05 mg/ml in the loading solution gives the best intensity and the least quenching. Less dye than 0.025 mg/ml gives less intensity and less quenching because the spacing of the dyes begins to significantly increase and more dye than 0.05 mg/ml gives less intensity and more quenching because of the increased closeness of the dyes in the particles. This type of experiment illustrates the procedure for optimization of fluorescence intensity and for minimizing quenching.

EXAMPLE 12
Verification of Fluorescence Energy Transfer in Latex Particles

The latex particles which were incorporated with various dyes for energy transfer were diluted to 0.06% to 0.001% solids in water and either tetrahydrofuran or dimethylformamide and the solutions of equal solids concentrations were excited at wavelengths which corresponded to the approximate excitation maximum of the donor dye. The particles were diluted into organic solvents in order to liberate the dyes from the latex, and therefore, disrupt any energy transfer process between the dyes in the particles. The fluorescence of the solutions in water and organic solvent at the emission maximum of the acceptor dye or dyes were recorded and compared. Fluorescence energy transfer was defined as significant when the emission intensity of the acceptor was at least 5-fold higher in water than in the organic solvent.

EXAMPLE 13
Effect of Varying Donor Dye Concentration With Respect to Acceptor Dye Concentration in Latex Particles on the Fluorescence Intensity of the Particles Meso-tetra 2-dimethylaminophenyl porphyrin was made as follows. To a stirring solution of meso tetra 2-aminophenyl porphyrin (100 mg, 0.15 mmol) and 37% aqueous formaldehyde (500 µL, 6.0 mmol) in tetrahydrofuran (2.5 ml was added sodium cyanoborohydride (114 mg, 1.8 mmol). The mixture was then treated with a glacial acetic acid (60 µL) over 10 minutes and stirred at room temperature for 3 hours. More glacial acetic acid (60 µL) was added and the mixture stirred a further 1 hour at room temperature. The mixture was evaporated and the residue was purified on a Silica gel to 60 column which was equilibrated in toluene. The product was eluted with tolene/ 1% isopropanol as a dark brown band. The fraction containing the product was evaporated and the ink-blue solid residue dried under vacuum to afford 85 mg of the title compound.

Meso-tetra-2-dimethylaminophenyl porphyrine (Tdap synthesized from the meso-tetra-2-aminophenylporphyrine which was obtained through Porphyrin Products, Inc. Logan, Utah) and PcSi vinyl (example 4) were incorporated into 67 nm latex particles (polystyrene sulfate latex from Interfacial Dynamics Inc., Portland, Oreg.) using the tetrahydrofuran method 1 of example 10. The molar ratio of the Tdap to the PcSi vinyl varied from 1/1 to 2/1 to 6/1 in the latex loading solutions while maintaining a constant mass (0.1 mg/ml) of PcSi vinyl in each solution. The dialyzed particles were diluted to 0.0019% solids in water and the fluorescence intensity at 680 nm of the PcSi vinyl was measured as a function of excitation wavelength between 350 nm and 470 nm. The excitation maximum of the Tdap is 430 nm and of the PcSi vinyl is 350 nm. The emission maximum of the Tdap is 650 nm. The table below shows the results.

| Tdap/PcSi vinyl | Excitation λ (nm) | Fluorescence Intensity at 680 nm |
|---|---|---|
| 1/1 | 350 | 490 |
| 1/1 | 430 | 83 |
| 1/1 | 450 | 38 |
| 1/1 | 470 | 11 |
| 2/1 | 350 | 580 |
| 2/1 | 430 | 830 |
| 2/1 | 450 | 460 |
| 2/1 | 470 | 220 |
| 6/1 | 350 | 600 |
| 6/1 | 430 | 1800 |
| 6/1 | 450 | 800 |
| 6/1 | 470 | 200 |

These results show that as the molar ratio of donor to acceptor in the latex particles increases from 1/1 to 6/1, the energy transfer, as measured by the fluorescence intensity of the acceptor dye, becomes significantly more efficient. There was no observable emission of the Tdap dye in the particles at the emission maximum of 650 nm suggesting that the energy transfer is very efficient. The data indicate that the fluorescence intensity of the latex particles, generated through an energy transfer pathway, is affected by the "light gathering" capability of the donor dye. Thus, optimization of the fluorescence intensity of the latex particles should involve changing the molar ratio of donor to acceptor.

EXAMPLE 14
Effect of Incorporation of Different Dyes on Quenching and Fluorescence Intensity of Latex Particles Five different silicon phthalocyanines, synthesized as described in examples 2–6, were incorporated into 67 nm surfactant-free, polystyrene latex particles (Interfacial Dynamics Corp. Inc. Portland, Oreg.) in sets of 1, 3 or 5 dyes according to the following methods. Each silicon phthalocyanine derivative had maximum excitation and emission wavelengths at 350 nm and 680 nm, respectively. After preparation of each dye-latex, each suspension was diluted to 0.059% solids in either water or tetrahydrofuran. The dye-latex solutions were excited at 350 nm and the fluorescence intensity at 680 nm was measured. The intensity of fluorescence in water divided by the intensity of fluorescence in tetrahydrofuran minus 1 is the degree of quenching of the dyes in the latex particles.

Preparation of One Phthalocyanine Dye in Latex

A solution of PcSi pentafluoro dye (0.02 mg) in tetrahydrofuran (0.1 ml) was added dropwise over 5 min to a stirred 2% solids solution of latex particles (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the solids concentration was adjusted to 1.6%.

Preparation of Three Phthalocyanine Dyes in Latex

A solution which consists of PcSi pentafluoro, PcSi trihexyl and PcSi cyano dyes in equimolar amounts to total 0.02 mg dye in tetrahydrofuran (0.1 ml), was added dropwise over 5 min to a stirred 2% solids solution of latex particles (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the solids concentration was adjusted to 1.6%.

Preparation of Five Phthalocyanine Dyes in Latex

A solution which consists of PcSi pentafluoro, PcSi trihexyl, PcSi cyano, PcSi vinyl and PcSi methyl ester dyes in equimolar amounts to total 0.02 mg dye in tetrahydrofuran (0.1 ml), was added dropwise over 5 min to a stirred 2% solids solution of latex particles solution (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 40° C. The dye-latex solutions were removed from dialysis and the % solids concentration was adjusted to 1.6%.

The table that follows illustrates the results of the fluorescence experiments.

| Dyes Entrapped | Intensity | % Quenching |
|---|---|---|
| 1 | 413 | 72 |
| 3 | 561 | 56 |
| 5 | 747 | 49 |

The data show that as the number of different dyes entrapped into the latex goes from 1 to 3 to 5, the fluorescence intensity increases because the quenching in the particles decreases.

EXAMPLE 15

Preparation and Characterization of Fluorescence Energy Transfer Dye Latex

A variety of fluorescent energy transfer latexes were prepared with various donor and acceptor dye molecules. Table 1 shows the loading concentrations of the respective donor and acceptor dyes, the mole ratio of the donor and acceptor dyes and the dye loading solvent system as described in Example 10. Table 2 shows the excitation and emission wavelengths and the fluorescence intensity for each particle size at the specified solids concentration for each dye system. The numbers 1–22 correlate in both Table 1 and Table 2 to the same dye systems. For some of the energy transfer latexes, the same dye pair was incorporated into different diameter latexes.

TABLE 1

| | DONOR DYE | LOADING CONC. (mg/mL) | ACCEPTOR DYE | LOADING CONC. mg/mL | MOLE DONOR: MOLE ACCEPTOR | SOLVENT SYSTEM |
|---|---|---|---|---|---|---|
| 1. | trans-4-[4-(Dibutyl amino)styryl]-1-methyl pyridinium Iodide | 0.120 mg/mL | Silicon phthalocyanine bis(di methylvinylsilyl oxide) | 0.100 mg/mL | 2:1 | THF |
| 2. | trans-4-[4-(Dibutyl amino)styryl]-1-methyl pyridinium Iodide | 0.100 mg/mL | Silicon 2,3-Napthalocyanine bis(di methylvinylsilyl oxide) | 0.230 mg/mL | 1:1 | DMF |
| 3. | trans-4-[4-(Dibutyl amino)styryl]-1-methyl pyridinium Iodide | 0.100 mg/mL | 1,1'-Dihexyl-3,3,3',3'-tetramethylindo-dicarbocyanine Iodide | 0.144 mg/mL | 1:1 | DMF |
| 4. | Meso-tetra-2-aminophenyl porphine | 0.180 mg/mL | Silicon phthalocyanine bis(di methylvinylsilyl oxide) | 0.100 mg/mL | 2:1 | THF |
| 5. | Meso-tetra-2-aminophenyl porphine | 0.100 mg/mL | 1,1'-Dihexyl-3,3,3',3'-tetramethylindodi-carbocyanine Iodide | 0.098 mg/mL | 1:1 | DMF |
| 6. | Meso-tetra-2-dimethyl aminophenyl porphine | 0.210 mg/mL | Silicon phthalocyanine bis(di methylvinylsilyl oxide) | 0.100 mg/mL | 2:1 | THF |
| 7. | 3-Ethyl-3'-ethyl carboxyethyl-thiacarbocyanine Iodide | 0.056 mg/mL | Silicon 2,3-Naphthalocyanine bis(di methylvinylsilyl oxide) | 0.250 mg/mL | 4:1 | DMF |
| 8. | 1,1'-Dioctadecyl-3,3,3',3'- | 0.036 mg/mL | Silicon 2,3-Naphthalocyanine bis(di | 0.0125 mg/mL | 4:1 | DMF |

TABLE 1-continued

| DONOR DYE | LOADING CONC. (mg/mL) | ACCEPTOR DYE | LOADING CONC. mg/mL | MOLE DONOR: MOLE ACCEPTOR | SOLVENT SYSTEM |
|---|---|---|---|---|---|
| tetramethyl indodicarbocyanine Perchlorate | | methylvinylsilyl oxide) | | | |
| 9. 1,1,-Diethyl-3,3,3',3'-tetramethyl indodicarbocyanine Iodide | 0.078 mg/mL | Silicon 2,3-Naphthalocyanine bis(di methylvinylsilyl oxide) | 0.025 mg/mL | 6:1 | DMF |
| 10. 1,1'-Dihexyl-3,3,3',3'-tetramethylindo dicarbocyanine Iodide | 0.094 mg/mL | Silicon 2,3-Naphthalocyanine bis(di methylvinylsilyl oxide) | 0.025 mg/mL | 6:1 | DMF |
| 11. 3,3'-Diethyl thiatricarbocyanine Iodide | 0.013 mg/mL | Silicon 2,3-Naphthalocyanine bis(di methylvinylsilyl oxide) | 0.025 mg/mL | 1:1 | DMF |
| 12. 3,3'-Dipropyl thiadicarbocyanine Iodide | 0.0131 mg/mL | Silicon 2,3-Naphthalocyanine bis(di methylvinylsilyl oxide) | 0.025 mg/mL | 1:1 | DMF |
| 13. 1,9-Dimethylmethylene blue, Chloride | .0083 mg/mL | Silicon 2,3-Naphthalocyanine bis(di methylvinylsilyl oxide) | 0.025 mg/mL | 1:1 | DMF |
| 14. N,N'-Di(3-trimethyl-ammoniumpropyl)thiadicarbo-cyanine Tribromide | 0.0129 mg/mL | Silicon 2,3-Naphthalocyanine bis(di methylvinylsilyl oxide) | 0.025 mg/mL | 1:1 | DMF |
| 15. 1,1',3,3,3',3'-Hexamethyl indotri-carbocyanine Perchlorate | 0.0122 mg/mL | Silicon 2,3-Naphthalocyanine bis(di methylvinylsilyl oxide) | 0.025 mg/mL | 1:1 | DMF |
| 16. N-(3-Triethyl-ammoniumpropyl)-4-(4-(p-dibutyl-aminophenyl) butadienyl) pyridium, Dibromide | 0.0143 mg/mL | Silicon 2,3-Naphthalocyanine bis(dimethyl-vinylsilyl oxide) | 0.025 mg/mL | 1:1 | DMF |
| 17. 1,1',3,3,3',3'-Hexamethyl-4,4'-5,5'-dibenzo-2,2' indotricarbo-cyanine Perchlorate | 0.0146 mg/mL | Silicon Naphthalocyanine bis(di methylvinylsilyl oxide) | 0.025 mg/mL | 1:1 | DMF |
| 18. Fluorescein | 0.264 mg/mL | Silicon phthalocyanine bis(di methylvinylsilyl oxide) | 0.100 mg/mL | 6:1 | THF |
| 19. Chlorophyll B | 0.0872 mg/mL | Silicon 2,3-Naphthalocyanine bis(di methylvinylsilyl oxide) | 0.025 mg/mL | 4:1 | THF |
| 20. Chlorophyll B | 0.244 mg/mL | Silicon phthalocyanine bis(di methylvinylsilyl oxide) | 0.100 mg/mL | 2:1 | THF |
| 21. trans-4-[4-(Dibutyl amino)styryl]-1-methyl pyridinium Iodide | 0.181 mg/mL | Silicon phthalocyanine bis(di methylpentafluoro-phenylsilyloxide) + Silicon | 0.070 mg/mL 0.050 mg/mL | 4:1:1 | THF |

TABLE 1-continued

| DONOR DYE | LOADING CONC. (mg/mL) | ACCEPTOR DYE | LOADING CONC. mg/mL | MOLE DONOR: MOLE ACCEPTOR | SOLVENT SYSTEM |
|---|---|---|---|---|---|
| 22. trans-4-[4-(Dibutyl amino)styryl]-1-methyl pyridinium Iodide | 0.072 mg/mL | phthalocyanine bis(di methylvinylsilyl oxide) Silicon phthalocyanine bis(tri hexylsilyloxide) + Silicon phthalocyanine bis(di methylpentafluoro-phenylsilyloxide) + Silicon phthalocyanine bis(di methylvinylsilyl oxide) | 0.040 mg/mL  0.040 mg/mL  0.030 mg/mL | 4:1:1:1 | THF |

TABLE 2

| DYE SYSTEM | EXCIT. (nm) | EMMIS. (nm) | PARTICLE SIZE ($\mu m$) | SOLIDS CONC. (%) | IN-TENSITY |
|---|---|---|---|---|---|
| 1 | 475 nm | 679 nm | 0.067 $\mu m$ | 0.0019% | 339.8 |
| 2 | 475 nm | 789 nm | 0.067 $\mu m$ | 0.057% | 347.1 |
| 3 | 475 nm | 688 nm | 0.067 $\mu m$ | 0.057% | 893.3 |
| 4 | 420 nm | 679 nm | 0.202 $\mu m$ | 0.0019% | 1020.0 |
| 4 | 420 nm | 679 nm | 0.587 $\mu m$ | 0.00095% | 1050.0 |
| 4 | 420 nm | 679 nm | 0.783 $\mu m$ | 0.00095% | 870.9 |
| 5 | 420 nm | 676 nm | 0.067 $\mu m$ | 0.0019% | 183.7 |
| 6 | 430 nm | 679 nm | 0.412 $\mu m$ | 0.0019% | 421.2 |
| 7 | 655 nm | 787 nm | 0.067 $\mu m$ | 0.057% | 287.3 |
| 8 | 650 nm | 787 nm | 0.067 $\mu m$ | 0.057% | 324.4 |
| 9 | 635 nm | 787 nm | 0.067 $\mu m$ | 0.057% | 742.6 |
| 9 | 635 nm | 787 nm | 0.412 $\mu m$ | 0.057% | 162.1 |
| 10 | 635 nm | 787 nm | 0.067 $\mu m$ | 0.057% | 907.4 |
| 10 | 635 nm | 787 nm | 0.412 $\mu m$ | 0.057% | 203.4 |
| 11 | 650 nm | 787 nm | 0.067 $\mu m$ | 0.057% | 11.7 |
| 12 | 655 nm | 787 nm | 0.067 $\mu m$ | 0.057% | 64.8 |
| 13 | 650 nm | 787 nm | 0.067 $\mu m$ | 0.057% | 57.4 |
| 14 | 645 nm | 787 nm | 0.067 $\mu m$ | 0.057% | 58.0 |
| 15 | 650 nm | 787 nm | 0.067 $\mu m$ | 0.057% | 33.2 |
| 16 | 500 nm | 787 nm | 0.067 $\mu m$ | 0.057% | 54.3 |
| 17 | 650 nm | 787 nm | 0.067 $\mu m$ | 0.057% | 7.5 |
| 18 | 485 nm | 683 nm | 0.067 $\mu m$ | 0.057% | 517.5 |
| 19 | 440 nm | 785 nm | 0.067 $\mu m$ | 0.057% | 72.2 |
| 20 | 440 nm | 682 nm | 0.067 $\mu m$ | 0.0019% | 139.1 |
| 21 | 475 nm | 681 nm | 0.067 $\mu m$ | 0.0019% | 300.2 |
| 22 | 475 nm | 681 nm | 0.067 $\mu m$ | 0.0019% | 206.4 |

EXAMPLE 16
Adsorption of Anti-human Chorionic Gonadotropin (hCG) Antibody to Latex Particles A typical example of the adsorptions of an antibody to dyed latex particles, prepared as described in Example 10, and of a complementary antibody to undyed latex particles, both of which can be used in a sandwich assay for hCG, is outlined below. Those skilled in the art will recognize that various techniques are available to adsorb or to covalently couple proteins, peptides, ligand analogues nucleotides and nucleic acids to latex particles.

A solution of dye latex (0.1 ml, 2% solids, 412 nm; entry 10, Table 1) was added quickly while vortexing to a solution of anti-B hCG monoclonal antibody (0.2 ml, 6.6 mg/ml; Applied Biotech Inc., San Diego, Calif.) in 20 mM sodium borate/150 mM sodium chloride, pH 8.2. A solution of 0.1 M potassium citrate, pH 3, (0.04 ml) was added quickly while vortexing to the antibody latex solution at room temperature and the pH of the resulting solution was 3.5. The solution incubated at room temperature for 5 min, then a solution of 2 M potassium borate, pH 9.7 (0.025 ml) was added quickly while vortexing to bring the pH to about 8.5. This latex antibody conjugate was dialyzed (Spectra-por dialysis tubing, molecular weight cutoff of 300,000, Spectrum, Houston, Tex.) against 4 changes of 2 1 each of 20 mM sodium borate/150 mM sodium chloride, pH 8.2 at 4° C. for 4 days. The dialyzed latex conjugate was then removed from the dialysis tubing and the solids concentration was calculated to be 0.4%. This conjugate can be used for immunoassays for hCG in serum. The latex has excitation and emission wavelengths of 650 nm and 780 nm, respectively.

A solution of polystyrene sulfate latex (0.036 ml, 8.4% solids, 1000 nm; Interfacial Dynamics Corp., Inc., Portland Oreg.) was added quickly, at room temperature, while vortexing to a solution consisting of anti-α hCG monoclonal antibody (0.12 ml, 10.3 mg/ml; Applied Biotech Inc. San Diego, Calif.) in 20 mM sodium borate/150 mM sodium chloride, pH 8.2 and 0.1 M potassium citrate, pH 3, (0.6 ml). The solution incubated at room temperature for 5 min and was subjected to centrifugation in an Eppendorf centrifuge (2000×g for 5 min). The supernatant was removed, the pellet was resuspended in 0.1 M potassium phosphate, pH 7, (1.5 ml) and the suspension was subjected to centrifugation as described above. This process was repeated 2 times more and in the final centrifugation, the pellet was resuspended with 0.1 M potassium phosphate, pH 7 (0.3 ml) to make 1% solids. This antibody latex is used on a solid phase, such as a membrane, to capture the hCG-dye antibody latex conjugate complex in a reaction mixture in an immunoassay for hCG.

EXAMPLE 17
Immunoassay for hCG

The solid phase anti-α hCG latex solution (0.005 ml, 1% solids; example 16) can be applied to a 2 cm² piece of 0.45 micron nylon membrane (Millipore Corp., Boston, Mass.) which has been treated with a 2% solution of condensed milk to lower non-specific binding interactions. This membrane can be used as the solid phase onto which is captured the hCG dye latex conjugate complex. Thus, an hCG assay can be performed by addition of dye latex conjugate (0.025 ml, example 16) to 0.1 ml samples of serum suspected of containing hCG and also to 0.1 ml serum samples containing known amounts of hCG (10, 100, 300, 500 and 1000 mIU/ml). The serum samples should be incubated about 10 min and then the samples are applied to the solid phase membrane containing the solid phase latex. The membrane should be placed over an absorbent so that the serum sample containing the dye latex conjugates flows through the solid phase latex spot. After the serum solution has passed through the membrane, serum (0.5 ml) not containing the dye latex conjugate is applied to the membrane to remove unbound dye latex conjugate. The latex spots on the membranes are then placed in a front surface fluorescence accessory in a fluorometer and the spot is excited at 650 nm and the fluorescence intensity of the spot on each membrane is measured at 780 nm. The fluorescence intensity as a function of the hGC concentrations of the known samples is plotted. The fluorescence intensities of the unknown hCG serum samples can be compared to the known hCG concentrations from the graph.

EXAMPLE 18
Fluorometer for Measuring Near Infrared Emitting Dyes

The dye sample (2 ml sample volume in a 10 mm×10 mm quartz cuvette) was excited by a diode laser (Sun Laser SL-6; 1=670±10 nm, 0.95 mW) which was filtered by a low-pass cutoff filter (Corion LS700, passes wavelengths less than 700 nm). Fluorescence emission was detected at 90° to the incident diode laser beam. The emitted light was collected and focused on a silicon photodiode (Melles Griot, Cat. #13DS1009) by a condenser consisting of two aspheric lenses (Melles Griot, Cat #01 LAG 119). A high-pass cutoff filter (Schott Glass RG715) in front of the Silicon photodiode blocked scattered laser light at 670 nm but passed emitted light at wavelengths larger than 715 nm. The photocurrent from the silicon photodiode was amplified and displayed by a current amplifier in nanoamps ("nA"), (Melles Griot, Cat. #13 AMP 003). In some instances, 12 nm band filters were placed in front of the silicon photodiode with center wavelengths at 730 nm, 790 nm, 850 nm, and 900 nm.

EXAMPLE 19
Synthesis of $SiNc[OSi(Ph)_2CH=CH_2]_2$

A suspension of silicon 2,3 naphthalocyanine dihydroxide (39 mg, 0.05 mmol) in DMF (0.5 mL) containing diphenylvinylchlorosilane (28 uL, 0.125 mmol) and imidazole (7 mg, 0.1 mmol) was stirred under argon at RT for 18 h. The reaction mixture was evaporated and the residue purified on a silica column equilibrating with hexane and eluting the product with toluene as a long green band. The toluene fraction containing the product was evaporated to afford 5 mg green solid.

EXAMPLE 20
Synthesis of $SiNc[OSi(Ph)_3]_2$

A suspension of silicon 2,3 naphthalocyanine dihydroxide (39 mg, 0.05 mmol) in DMF (1 mL) containing triphenylchlorosilane (37 mg, 0.125 mmol) and imidazole (7 mg, 0.1 mmol) was stirred under argon at RT for 18 h. The reaction mixture was evaporated and the residue purified on a silica column equilibrating with hexane and eluting the product with toluene as a green band. The toluene fraction containing the product was evaporated to afford 2.5 mg green solid.

EXAMPLE 21
Synthesis of $SiNc[OSi(CH_3)_2O(CH_2)_2maleimide]_2$

A suspension of silicon 2,3 naphthalocyanine dihydroxide (39 mg, 0.05 mmol) in DMF (1 mL) containing dichlorodimethylsilane (13.5 uL, 0.11 mmol) and imidazole (14 mg, 0.2 mmol) was stirred under argon at RT for 18 h. The reaction mixture was then treated with N-(2-hydroxyethyl)maleimide (35 mg, 0.25 mmol) and stirred for additional 10 h. The reaction mixture was evaporated and the residue purified on a silica column equilibrating with hexane, then toluene and eluting the product with toluene/10% IPA as a green band. The eluate containing the product was evaporated to afford 3.5 mg of green solid.

EXAMPLE 22
Synthesis of $SiNc[OSi(CH_3)_2OPhCH=CHPh]_2$

A suspension of silicon 2,3 naphthalocyanine dihydroxide (39 mg, 25 0.05 mmol) in DMF (1 mL) containing dichlorodimethylsilane (13.5 uL, 0.11 mmol) and imidazole (14 mg, 0.2 mmol) was stirred under argon at RT for 2 h. The reaction mixutre was then treated with trans-4-hydroxystilbene (49 mg, 0.25 mmol) and stirred for additional 5 h. The reaction mixture was evaporated and the residue purified on a silica column equilibrating with hexane and eluting the product with toluene as a long green band. The toluene fraction containing the product was evaporated to afford 4 mg green solid.

EXAMPLE 23
Synthesis of $SiNc[OSi(CH_3)_2(CH_2)_6CH=CH_2]_2$

A suspension of silicon 2,3 naphthalocyanine dihydroxide (39 mg, 0.05 mmol) in DMF (1 mL) containing 7-oct-1-enyldimethylchlorosilane (32 uL, 0.125 mmol) and imidazole (7 mg, 0.1 mmol) was stirred under argon at RT for 18 h. The reaction mixture was evaporated and the residue purified on silica column equilibrating with hexane and eluting the product with toluene as a green band. The toluene fraction containing the product was evaporated and the residue treated with hexane to afford a dark green solid and light green supernatant. The mixture was centrifuged, the supernatant removed and the solid treated with more hexane and centrifuged. The supernatant was again removed and the solid dried under vacuum to yield 7.3 mg of product.

EXAMPLE 24
Synthesis of $SiNc[OSi(CH_3)_2(CH_2)_2C_6F_{13}]_2$

A suspension of silicon 2,3 naphthalocyanine dihydroxide (39 mg, 0.05 mmol) in DMF (1 mL) containing (tridecafluoro-1,1,2,2-tetrahydrooctyl)-1-dimethylchlorosilane (37 uL, 0.1 mmol) and imidazole (7 mg, 0.1 mmol) was stirred under argon at RT for 2 h. The reaction mixture was evaporated and the residue purified on a silica column equilibrating with hexane and eluting with hexane/20% toluene followed by hexane/40% toluene to afford the product as a green band. The product eluate was evaporated and the residue treated with hexane to afford a green solid. The mixture was centrifuged, the supernatant removed and the solid treated with more hexane and recentrifuged. The supernatant was again removed and the green solid dried under vacuum to yield 7.5 mg of product.

EXAMPLE 25
Synthesis of $SiNc[OSi(CH_3)_2O$-retinol$]_2$

A suspension of silicon 2,3 naphthalocyanine dihydroxide (39 mg, 0.05 mmol) in DMF (1 mL) containing dichlorodimethylsilane (13.5 uL, 0.11 mmol) and imidazole (14 mg, 0.2 mmol) was stirred under argon at RT. After 20 minutes, the reaction mixture was treated with all-trans-retinol (72 mg, 0.25 mmol) and stirred for an additional 1 h. The reaction mixture was evaporated and the residue purified on a silica column equilibrating with hexane and eluting the product with toluene as a long green band. The toluene fraction containing the product was evaporated and the residue treated with hexane to yield a dark green solid and light green supernatant. The mixture was centrifuged, the hexane removed and the solid dried under vacuum to yield 10 mg of final product.

EXAMPLE 26
Synthesis of $SiNc(OEt)_8Cl_2$ 4,9-Diethoxy-1,3-diiminobenz[f]isoindoline (0.6 gm, 2.1 mmol) was added under argon to a solution of quinoline (12 mL). After stirring for 10 minutes, silicon tetrachloride (4.0 mL, 35 mmol) was added and the reaction mixture was heated at 190 C. for 1 h. The reaction mixture was cooled to RT, and water (120 mL) was added slowly to hydrolyze the unreacted silicon tetrachloride. The blue-black precipitate was filtered off and washed with methanol and acetone.

EXAMPLE 27
Synthesis of $SiNc(OEt)_8(OH)_2$

A suspension of $SiNc(OEt)_8Cl_2$ (1.96 gm, 1.7 mmol) in pyridine (15 mL) containing water (15 mL) was refluxed with stirring in an oil bath at 130 C. for 18 h. The suspension was cooled, the black precipitate filtered and washed with water (10 mL). The ppt was dried under vacuum over the weekend to afford 1.37 gm of purple powder.

EXAMPLE 28
Synthesis of $SiNc(OEt)_8[OSi(CH_3)_2(CH_2)_6CH=CH_2]_2$

A suspension of $SiNc(OEt)_8(OH)_2$ (1.0 gm, 0.9 mmol) in DMF (20 mL) containing 7-oct-1-enyldimethylchlorosilane (0.6 mL, 2.3 mmol) and imidazole (140 mg, 2.1 mmol) was stirred under argon at RT for 24 h. The reaction mixture was evaporated and redissoved in hexane. The solution was purified on a silica gel column equilibrating with hexane and eluting the product with toluene/hexane (1:1). The eluate was evaporated to yield 46 mg of final product.

EXAMPLE 29
Synthesis of $SiPc[OSi(CH_3)_2maleimide-fluorescein]_2$

Fluorescein ATP (0.5 mg, 1.05 umol) was treated with a solution of 0.12M potassium carbonate in 80% methanol (52 uL). After 5 minutes, the hydrolysis solution was quenched by the addition of 0.5 M potassium phosphate/0.1 M potassium borate, pH 7.0 in 1 N HCl(10 uL). The quenched hydrolysis solution was evaporated to dryness, redissolved in DMF(100 uL) and the resulting solution added to SiPc $[OSi(CH_3)_2$ maleimide$]_2$ in a 1.0 mL serum vial. The reaction was then stirred at RT for 1 h. The crude product was then chromatographed on two 3"×3" silica plates using toluene/20% DMF. After elution, the plates were dried under vacuum and rechromatographed for a better separation. The product band was scraped off, and treated with DMF (5 mL), vortexed 30 seconds and filtered from the silica. The filtrates were evaporated to give 0.55 mg of greenish fluorescent solid.

EXAMPLE 30
Description of Donor/Acceptor Dye Pairs

A chart depicting donor/acceptor dye pairs and their fluorescence properties follows.

| DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 1. trans-4-[4-(Dibutyl amino)styryl]-1-methyl pyridinium Iodide | 0.120 mg/mL | Silicon phthalocyanine bis(di methylvinylsilyloxide) | 0.100 mg/mL | 2:1 | THF (0.067 μm) | 340 (0.0019%) | 679 nm (475 nm) |
| 2. trans-4-[4-(Dibutyl amino)styryl]-1-methyl pyridinium Iodide | 0.100 mg/mL | Silicon 2,3- Napthalocyanine bis(di methylvinylsilyloxide) | 0.230 mg/mL | 1:1 | DMF (0.067 μm) | 347 (0.057%) | 789 nm (475 nm) |
| 3. trans-4-[4-(Dibutyl amino)styryl]-1-methyl pyridinium Iodide | 0.100 mg/mL | 1,1'-Dihexyl-3,3,3',3'-tetramethylindodicarbo-cyanine Iodide | 0.144 mg/mL | 1:1 | DMF (0.067 μm) | 688 (0.057%) | 688 nm (645 nm) |
| 4. Meso-tetra-2-aminophenyl porphine | 0.100 mg/mL | Silicon phthalocyanine bis(di methylvinylsilyloxide) | 0.100 mg/mL | 2:1 | THF (0.202 μm) | 1000 (0.00095%) | 679 nm (420 nm) |
| 5. Meso-tetra-2-aminophenyl porphine | 0.100 mg/mL | 1,1'-Dihexyl-3,3,3',3'-tetramethylindodicarbo-cyanine Iodide | 0.098 mg/mL | 1:1 | DMF (0.067 μm) | 157 (0.0.0019%) | 676 nm (645 nm) |
| 6. Meso-tetra-2-dimethyl aminophenyl porphine | 0.210 mg/mL | Silicon phthalocyanine bis(di methylvinylsilyloxide) | 0.100 mg/mL | 2:1 | THF (0.412 μm) | 209 (0.00095%) | 679 nm (430 nm) |
| 7. 3-Ethyl-3'-ethyl carboxyethylthia-carbocyanine Iodide | 0.056 mg/mL | Silicon 2,3- Napthalocyanine bis(di methylvinylsilyloxide) | 0.250 mg/mL | 4:1 | DMF (0.067 μm) | 289 (0.057%) | 785 nm (650 nm) |
| 8. 1,1'-Dioctadecyl-3,3,3,3',3'-tetramethyl indodi-carbocyanine Perchlorate | 0.036 mg/mL | Silicon 2,3- Napthalocyanine bis(di methylvinylsilyloxide) | 0.0125 mg/mL | 4:1 | DMF (0.067 μm) | 324 (0.057%) | 787 nm (650 nm) |
| 9. 1,1'-Diethyl-3,3,3',3'-tetramethyl indodi-carbocyanine Iodide | 0.078 mg/mL | Silicon 2,3- Napthalocyanine bis(di methylvinylsilyloxide) | 0.025 mg/mL | 6:1 | DMF (0.067 μm) | 723 (0.057%) | 787 nm (635 nm) |

-continued

| | DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|---|
| 10. | 1,1'-Dihexyl-3,3,3',3'-tetramethylindodicarbocyanine Iodide | 0.094 mg/mL | Silicon 2,3-Napthalocyanine bis(dimethylvinylsilyloxide) | 0.025 mg/mL | 6:1 | DMF (0.067 μm) | 907 (0.057%) | 783 nm (635 nm) |
| 11. | 3,3'-Diethyl thiatricarbocyanine Iodide | 0.013 mg/mL | Silicon 2,3-Napthalocyanine bis(dimethylvinylsilyloxide) | 0.025 mg/mL | 1:1 | DMF (0.067 μm) | 12 (0.057%) | 788 nm (650 nm) |
| 12. | 3,3'-Dipropyl thiadicarbocyanine Iodide | 0.0131 mg/mL | Silicon 2,3-Napthalocyanine bis(dimethylvinylsilyloxide) | 0.025 mg/mL | 1:1 | DMF (0.067 μm) | 65 (0.057%) | 788 nm (660 nm) |
| 13. | 1,9-Dimethylmethylene blue, Chloride | .0083 mg/mL | Silicon 2,3-Napthalocyanine bis(dimethylvinylsilyloxide) | 0.025 mg/mL | 1:1 | DMF (0.067 μm) | 57 (0.057%) | 788 nm (650 nm) |
| 14. | N,N'-Di(3-tri methylammoniumpropyl) thia-dicarbocyanine Tribromide | 0.0129 mg/mL | Silicon 2,3-Napthalocyanine bis(dimethylvinylsilyloxide) | 0.025 mg/mL | 1:1 | DMF (0.067 μm) | 63 (0.057%) | 788 nm (650 nm) |
| 15. | 1,1',3,3',3'-Hexamethyl indotricarbocyanine Perchlorate | 0.0122 mg/mL | Silicon 2,3-Napthalocyanine bis(dimethylvinylsilyloxide) | 0.025 mg/mL | 1:1 | DMF (0.067 μm) | 33 (0.057%) | 788 nm (650 nm) |
| 16. | N-(3-Triethylammonium-propyl)-4-4-(p-dibutylaminophenyl) butadienyl)pyridium, Dibromide | 0.0143 mg/mL | Silicon 2.3-Napthalocyanine bis(dimethylvinylsilyloxide) | 0.025 mg/mL | 1:1 | DMF (0.067 μm) | 55 (0.057%) | 788 nm (500 nm) |
| 17. | 1,1',3,3',3'-Hexamemethyl-4,4'-5,5'-dibenzo-2,2' indotricarbocyanine Perchlorate | 0.0146 mg/mL | Silicon 2.3-Napthalocyanine bis(dimethylvinylsilyloxide) | 0.025 mg/mL | 1:1 | DMF (0.067 μm) | 8 (0.057%) | 788 nm (650 nm) |
| 18. | Fluoroscein | 0.264 mg/mL | Silicon phthalocyanine bis(dimethylvinylsilyloxide) | 0.100 mg/mL | 6:1 | THF (0.067 μm) | 517 (0.057%) | 683 nm (485 nm) |
| 19. | Chlorophyll B | 0.0872 mg/mL | Silicon 2,3-Napthalocyanine bis(dimethylvinylsilyloxide) | 0.025 mg/mL | 4:1 | THF (0.067 μm) | 72 (0.057%) | 783 nm (440 nm) |
| 20. | Chlorophyll B | 0.244 mg/mL | Silicon phthalocyanine bis(dimethylvinylsilyloxide) | 0.100 mg/mL | 2:1 | THF (0.067 μm) | 140 (0.0019%) | 679 nm (440 nm) |
| 21. | trans-4-[4-(Dibutyl amino)styryl]-1-methyl pyridinium Iodide | 0.181 mg/mL | Silicon phthalocyanine bis(dimethylpentafluorophenylsilyl-oxide) + Silicon phthalocyanine bis(dimethylvinylsilyloxide) | 0.070 mg/mL<br>0.050 mg/mL | 4:1:1 | THF (0.067 μm) | 300 (0.0019%) | 681 nm (475 nm) |
| 22. | trans-4-[4-(Dibutyl amino)styryl]-1-methyl pyridinium Iodide | 0.072 mg/mL | Silicon phthalocyanine bis(trihexylsilyloxide) + Silicon phthalocyanine bis(dimethylpentafluorophenylsilyl-oxide) + Silicon phthalocyanine bis(dimethylvinylsilyloxide) | 0.040 mg/mL<br>0.040 mg/mL<br>0.030 mg/mL | 4:1:1:1 | THF (0.067 μm) | 206 (0.0019%) | 681 nm (475 nm) |
| 23. | 3-Ethyl-3'-carboxyethylthiadi-carbocyanine iodide | 0.013 mg/mL | Silicon 2,3-Naphthalocyanine bis(dimethylvinylsilyloxide) | 0.025 mg/mL | 1:1 | DMF (0.067 μm) | 76 (0.057%) | 788 nm (625 nm) |
| 25. | 3-Ethyl-3'-ethylcarboxyethyloxa-thiadicarbocyanine iodide | 0.013 mg/mL | Silicon 2,3-Naphthalocyanine bis(dimethylvinylsilyloxide) | 0.025 mg/mL | 1:1 | DMF (0.067 μm) | 135 (0.057%) | 788 nm (630 nm) |
| 26. | 3,3'-Diethylthiadi-carbocyanine iodide | 0.013 mg/mL | Silicon 2,3-Naphthalocyanine bis(dimethylvinylsilyloxide) | 0.025 mg/mL | 1:1 | DMF (0.067 μm) | 59 (0.057%) | 787 nm (660 nm) |
| 27. | 3,3'-Diethyloxadi-carbocyanine Iodide | 0.012 mg/mL | Silicon 2,3-Naphthalocyanine bis(dimethylvinylsilyloxide) | 0.025 mg/mL | 1:1 | DMF (0.067 μm) | 57 (0.057%) | 787 nm (590 nm) |
| 28. | 1,1'-Dihexyl-3,3,3',3'-tetramethylindodicarbo-cyanine iodide | 0.094 mg/mL | Silicon 2,3-Naphthalocyanine bis(dimethylvinylsilyloxide) + Silicon napthalocyanine bis(dimethylethylmaleimide-silyloxide) | 0.025 mg/mL<br>0.05 mg/mL | 6:1:2 | DMF (0.431 μm CML) | 127 (0.057%) | 788 nm (650 nm) |

-continued

| DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 29. 1,1'-Dihexyl-3,3,3',3'-tetramethylindodicarbo-cyanine Iodide | 0.094 mg/mL | Silicon 2,3-Naphthalocyanine bis(dimethylvinylsilyloxide) + Silicon phthalocyanine bis(dimethylethylmaleimide-silyloxide) | 0.025 mg/mL  0.05 mg/mL | 6:1:2 | DMF (0.431 μm CML) | 193 (0.057%) | 788 nm (650 nm) |
| 30. 1,1'-Dihexyl-3,3,3',3'-tetramethylindodicarbo-cyanine Iodide | 0.030 mg/mL | Silicon 2,3-Naphthalocyanine bis(dimethylhexylvinylsilyl oxide) | 0.05 mg/mL | 1:1 | DMF (0.431 μm CML) | 275 (0.057%) | 788 nm (650 nm) |
| 31. 1,1'-Dihexyl-3,3,3',3'-tetramethylindodicarbo-cyanine Iodide | 0.10 mg/mL | Silicon Napthalocyanine bis(dimethyltriphenylsilyl-oxide) | 0.20 mg/mL | 1:1 | DMF (0.431 μm CML) | 163 (0.057%) | 798 nm (650 nm) |
| 32. 1,1'-Dihexyl-3,3,3'.3'-tetramethylindodicarb-cyanine Iodide | 0.09 mg/mL | Silicon Napthalocyanine bis(dimethylretinol) | 0.05 mg/mL | 4:1 | DMF (0.431 μm CML) | 153 (0.057%) | 790 nm (650 nm) |
| 33. 1,1',3,3,3',3'-Hexamethylindotricarbo-cyanine Perchlorate | 0.216 mg/mL | Silicon 2,3-Naphthalocyanine bis(dimethylvinylsilyloxide) | 0.1 mg/mL | 4:1 | DMF (0.431 μm CML) | 0.4 (0.00067%) | 788 nm (635 nm) |
| 34. 1,1'-Dihexyl-3,3,3',3'-tetramethylindodicarbo-cyanine Iodide | 0.512 mg/mL | 1,1',3,3,3',3'-Hexamethylindotricarbo-cyanine Perchlorate | 0.1 mg/mL | 4:1 | DMF (0.431 μm CML) | 0.9 (0.00057%) | 776 nm (635 nm) |
| 35. [(C$_6$H$_5$C≡C)$_4$B]⁻Li⁼ | 0.160 mg/mL | Silicon 2,3-Napthalocyanine bis(dimethylhexylvinylsilyl oxide) | 0.1 mg/mL | 4:1 | DMF (0.216 μm CML) | 22 (0.00057%) | 788 nm (635 nm) |
| 36. Silicon phthalocyanine bis(dimethylvinylsilyloxide) | 0.334 mg/mL | Silicon 2,3-Napthalocyanine bis(dimethylhexylvinylsilyl oxide) | 0.I mg/mL | 10:1 | DMF (0.216 μm CML) | 1 (000057%) | 800 nm (650 nm) |
| 37. 1,1',3,3,3',3'-Hexamethylindotricarbo-cyanine Perchlorate | 0.23 mg/mL | Silicon 2,3-Napthalocyanine bis(dimethylhexylvinylsilyl oxide) | 0.1 mg/mL | 10:1 | DMF (0.216 μm CML) | 0.4 (0.00057%) | 780 nm (635 nm) |
| 38. 1,1',3,3,3',3'-Hexamethylindotricarbo-cyanine Perchlorate | 0.19 mg/mL | SiNc(EtO)$_8$[OSi(CH$_3$)$_2$(CH$_2$)$_6$CH=CH$_2$]$_2$ | 0.1 mg/mL | 10:1 | DMF (0.216 μm CML) | 0.7 (0.00057%) | 780 nm (635 nm) |
| 39. Oxazine 1 Perchlorate | 0.01 mg/mL | Silicon 2,3-Napthalocyanine bis(dimethylvinylsilyloxide) | 0.025 mg/mL | 1:1 | DMF (0.067 μm) | 291 (0.057%) | 788 nm (650 nm) |
| 40. 1,1'-Dihexyl-3,3,3',3'-tetramethylindodicarbo-cyanine Iodide | 0.12 mg/mL | Octabutoxyphthalocyanine | 0.1 mg/ml | 4:1 | DMF (0.431 μm CML) | 0 | 0 |
| 41. 3,3'-Dipropylthiadicarbocyanine Iodide | 0.232 mg/mL | Silicon 2,3-Napthalocyanine bis(dimethylvinylsilyloxide) | 0.1 mg/mL | 4:1 | DMF (0.431 μm CML) | 0.4 (0.00057%) | 788 nm (635 nm |
| 42. Copper phthalocyanine (4-tert-Butyl)$_4$ | 0.72 mg/mL | Silicon 2,3-Napthalocyanine bis(dimethylhexylvinylsilyl oxide) | 0.1 mg/mL | 1:1 | DMF (0.216 μm CML) | 0.2 (0.00057%) | 788 nm (650 nm) |
| 43. (E,E)-3,5-bis-(4-phenyl-1,3-butadienyl)-4,4-difluoro-4-bora-3a,4a-diazo-s-indacene | .16 mg/mL | Silicon 2,3-Napthalocyanine bis(dimethylhexylvinylsilyl oxide) | 0.1 mg/mL | 4:1 | DMF (0.216 μm CML) | 42 (0.00057%) | 785 nm (670 nm) |
| 44. Aluminum Phthalocyanine Hydroxyl (4-tert-butyl)$_4$ | 0.28 mg/mL | Silicon 2,3-Napthalocyanine bis(dimethylhexylvinylsilyl oxide) | 0.1 mg/mL | 4:1 | THF (0.216 μm CML) | 0.5 (0.00057%) | 788 nm (650 nm) |
| 45. Aluminum Phthalocyanine Chloride (4-tert-butyl)$_4$ | 0.29 mg/mL | Silicon 2,3-Napthalocyanine bis(dimethylhexylvinylsilyl oxide) | 0.1 mg/mL | 4:1 | DMF (0.216 μm CML) | 0.1 (0.00057%) | 788 nm (650 nm) |
| 46. (E,E)-3,5-bis-(4-phenyl-1,3-butadienyl)-4,4-difluoro-4-bora-3a,4a-diazo-s-indacene | 0.14 mg/mL | Aluminum Phthalocyanine Octabutoxy triethylsilyloxide | 0.1 mg/mL | 4:1 | THF (0.216 μm CML) | 1.8 (0.00057%) | 774 nm (650 nm) |
| 47. Iron Phthalocyanine (CN-tert-butyl)$_4$ | 0.26 mg/mL | Silicon 2,3-Napthalocyanine bis(dimethylhexylvinylsilyl oxide) | 0.1 mg/mL | 4:1 | THF (0.216 μm CML) | 0.3 (0.00057%) | 788 nm (670 nm) |

-continued

| DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 48. (E,E)-3,5-bis-(4-phenyl-1,3-butadienyl)-4,4-difluoro-4-bora-3a,4a-diazo-s-indacene | 0.16 mg/mL | Phthalocyanine Octabutoxy | 0.1 mg/mL | 4:1 | THF (0.216 μm CML) | 0.7 (0.00057%) | 783 nm (670 nm) |
| 50. (E,E)-3,5-bis-(4-phenyl-1,3-butadienyl)-4,4-difluoro-4-bora-3a,4a-diazo-s-indacene | 0.15 mg/mL | Silicon 2,3-Napthalocyanine bis(dimethylphenylpentafluorosilyloxide) | 0.1 mg/mL | 4:1 | THF (0.216 μm CML) | 16.9 (0.00057%) | 783 nm (670 nm) |
| 51. (E,E)-3,5-bis-(4-phenyl-1,3-butadienyl)-4,4-difluoro-4-bora-3a,4a-diazo-s-indacene | 0.19 mg/mL | Silicon 2,3-Napthalocyanine bis(dimethylvinylsilyloxide) | 0.1 mg/mL | 4:1 | THF (0.216 μm CML) | 31.5 (0.00057%) | 783 nm (670 nm) |
| 52. (E,E)-3,5-bis-(4-phenyl-1,3-butadienyl)-4,4-difluoro-4-bora-3a,4a-diazo-s-indacene | 0.15 mg/mL | Silicon 2,3-Napthalocyanine bis(diphenylvinylsilyloxide) | 0.1 mg/mL | 4:1 | THF (0.216 μm CML) | 13.1 (0.00057%) | 783 nm (670 nm) |
| 53. (E,E)-3,5-bis-(4-phenyl-1,3-butadienyl)-4,4-difluoro-4-bora-3a,4a-diazo-s-indacene | 0.15 mg/mL | Silicon 2,3-Napthalocyanine $[OSi(CH_3)_2O(CH_2)_2mal]_2$ | 0.1 mg/mL | 4:1 | THF (0.216 μm CML) | 4.7 (0.00057%) | 783 nm (670 nm) |
| 54. (E,E)-3,5-bis-(4-phenyl-1,3-butadienyl)-4,4-difluoro-4-bora-3a,4a-diazo-s-indacene | 0.14 mg/mL | Silicon 2,3-Napthalocyanine $[OSi(CH_3)_2O-Ph=Ph]_2$ | 0.1 mg/mL | 4:1 | THF (0.216 μm CML) | 11.7 (0.00057%) | 783 nm (670 nm) |
| 55. (E,E)-3,5-bis-(4-phenyl-1,3-butadienyl)-4,4-difluoro-4-bora-3a,4a-diazo-s-indacene | 0.12 mg/mL | Silicon 2,3-Napthalocyanine $[OSi(CH_3)_2(CH_2)_2C_6F_{13}]_2$ | 0.1 mg/mL | 4:1 | THF (0.216 μm CML) | 22.3 (0.00057%) | 783 nm (670 nm) |
| 56. (E,E)-3,5-bis-(4-phenyl-1,3-butadienyl)-4,4-difluoro-4-bora-3a,4a-diazo-s-indacene | 0.12 mg/mL | Silicon 2,3-Napthalocyanine bis(dimethylretinol) | 0.1 mg/mL | 4:1 | THF (0.216 μm CML) | 16.1 (8.00057%) | 783 nm (670 nm) |
| 57. Germanium Phthalocyanine $(OH)_2(t-Bu)_4$ | 0.3 mg/mL | Silicon 2,3-Napthalocyanine bis(dimethylhexylvinylsilyl oxide) | 0.1 mg/mL | 4:1 | THF (0.216 μm CML) | 1.3 (0.00057%) | 783 nm (670 nm) |
| 58. Germanium Phthalocyanine $(Cl)_2(t-Bu)_4$ | 0.3 mg/mL | Silicon 2,3-Napthalocyanine bis(dimethylhexylvinylsilyl oxide) | 0.1 mg/mL | 4:1 | THF (0.216 μm CML) | 0.6 (0.00057%) | 783 nm (670 nm) |
| 59. Silicon Phthalocyanine (maleimide-fluoroscein)$_2$ FET COMPOUN0 | 0.15 mg/mL | Silicon Phthalocyanine (maleimide-fluoroscein)$_2$ FET COMPOUN0 | | | THF (0.067 μm) | 209 (0.0019%) | 681 nm (470 nm) |
| 60. 5,5'-Dichloro-1,1'-diphenylamino-3,3'-diethyl-10,12-ethylenethiatricarbocyanine Iodide | 0.57 mg/mL | 3,3'-Diethylthiatricarbocyanine Iodide | 0.1 mg/mL | 4:1 | DMF (0.216 μm CML) | −0.56 nA (0.00057%) | (670 nm) |
| 61. 5,5'-Dichloro-1,1'-diphenylamino-3,3'-diethyl-10,12-ethylenethiatricarbocyanine Iodide | 0.61 mg/mL | 1,1',3,3,3',3'-Hexamethylindotricarbocyamine Perchlorate | 0.1 mg/mL | 4:1 | DMF (0.216 μm CML) | −0.048 nA (0.00057%) | (670 nm) |
| 62. 5,5'-Dichloro-1,1'-diphenylamino-3,3'-diethyl-10,12-ethylenethiatricarbocyanine Iodide | 0.51 mg/mL | 1,1',3,3,3',3'-Hexamethyl-4,4',5,5'-dibenzo-2,2'-indotricarbocyanine Perchlorate | 0.1 mg/mL | 4:1 | DMF (0.216 μm CML) | −0.149 nA (0.00057%) | (670 nm) |
| 63. 1,1'-Dihexyl-3,3,3',3'-tetramethylindodicarbocyanine Iodide | 0.23 mg/mL | Silicon 2,3-Napthalocyanine bis(dimethylhexylvinylsilyl oxide) | 0.1 mg/mL | 4:1 | DMF (0.216 μm CML) | −14.12 nA (0.00057%) | (670 nm) |
| 64. (E,E)-3,5-bis-(4-phenyl-1,3-butadienyl)-4,4-difluoro-4-bora-3a,4a-diazo-s-indacene | 0.16 mg/mL | Silicon 2,3-Napthalocyanine bis(dimethylhexylvinylsilyl oxide) | 0.1 mg/mL | 4:1 | DMF (0.216 μm CML) | −5.00 nA (0.00057%) | (670 nm) |
| 65. (E,E)-3,5-bis-(4-phenyl-1,3-butadienyl)-4',4-difluoro-4-bora-3a,4a-diazo-s-indacene | 0.26 mg/mL | $SiNc(EtO)_8[OSi(CH_3)_2(CH_2)_6CH=CH_2]_2$ | 0.1 mg/mL | 4:1 | DMF (0.216 μm CML) | −2.74 nA (0.00057%) | (670 nm) |

-continued

| DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 66. (E,E)-3.5-bis-(4-phenyl-1,3-butadienyl)-4,4-difluoro-4-bora-3a,4a-diazo-s-indacene | 0.32 mg/mL | Phthalocyanine Octabutoxy | 0.1 mg/mL | 4;1 | DMF (0.216 μm CML) | −4.07 nA (0.00057%) | (670 nm) |
| 67. (E,E)-3,5-bis-(4-phenyl-1,3-butadienyl)-4,4-difluoro-4-bora-3a,4a-diazo-s-indacene | 0.28 mg/mL | Napthalocyanine Octabutoxy | 0.1 mg/mL | 4:1 | DMF (0.216 μm CML) | −1.76 nA (0.00057%) | (670 nm) |
| 68. 1,1′-Dihexyl-3,3,3′,3′-tetramethylindocarbocyanine Iodide | 0.19 mg/mL | $SiNc(EtO)_6[OSi(CH_3)_2(CH_2)_6CH=CH_2]_2$ | 0.1 mg/mL | 4:1 | DMF (0.216 μm CML) | −0.712 nA (000057%) | (670 nm) |
| 69. 3,3′-Diethyl-thiatricarbocyanine Iodide | 0.16 mg/mL | $SiNc(EtO)_6[OSi(CH_3)_2(CH_2)_6CH=CH_2]_2$ | 0.1 mg/mL | 4:1 | DMF (0.216 μm CML) | −0.058 nA (0.00057%) | (670 nm) |
| 70. 1,1′,3,3,3′,3′-Hexamethylindotricarbocyanine Perchlorate | 0.15 mg/mL | $SiNc(EtO)_6[OSi(CH_3)_2(CH_2)_6CH=CH_2]_2$ | 0.1 mg/mL | 4:1 | DMF (0.216 μm CML) | −0.141 nA (0.00057%) | (670 nm) |
| 71. 1,1′,3,3,3′,3′-Hexamethyl-4,4′,5,5′-dibenzo-2,2′-indotricarbocyanine Perchlorate | 0.19 mg/mL | $SiNc(EtO)_6[OSi(CH_3)_2(CH_2)_6CH=CH_2]_2$ | 0.1 mg/mL | 4:1 | DMF (0.216 μm CML) | −0.058 nA (0.00057%) | (670 nm) |
| 72. (E,E)-3,5-bis-(4-phenyl-1,3-butadienyl)-4,4-difluoro-4-bora-3a,4a-diazo-s-indacene | 0.2 mg/mL | Silicon 2,3-Napthalocyanine bis(dimethylhexylvinylsilyl oxide) Octaethoxy | 0.15 mg/mL | 4:1 | THF (0.216 μm CML) | −2.720 nA (0.00057%) | (670 nm) |
| 73. (E,E)-3,5-bis-(4-phenyl-1,3-butadienyl)-4,4-difluoro-4-bora-3a,4a-diazo-s-indacene | 0.16 mg/mL | Silicon 2,3-Napthalocyanine bis(dimethylhexylvinylsilyl oxide) + Silicon 2,3-Napthalocyanine bis(dimethylhexylvinylsilyl oxide) Octaethoxy | 0.1 mg/mL  0.12 mg/mL | 4:1:1 | THF (0.216 μm CML) | −2.38 nA (0.00057%) | (670 nm) |
| 74. Silicon Phthalocyanine bis(dimethylvinylsilyloxide) | 0.36 mg/mL | 5,5′-Dichloro-1,1′-diphenylamino-3,3′-diethyl-10,12-ethylenethiatricarbocyanine Perchlorate | 0.1 mg/mL | 4:1 | THF (0.216 μm CML) | −8.10 nA (0.0057%) | (670 nm) |
| 75. Tetrakis(4-cumylphenoxy) Phthalocyanine | 0.48 mg/mL | Silicon 2,3-Napthalocyanine bis(dimethylhexylvinylsilyl oxide) | 0.1 mg/mL | 4:1 | THF (0.216 μm CML) | −0.397 nA (0.00057%) | (670 nm) |
| 76. Tetrakis(4-cumylphenoxy) Phthalocyanine | 0.68 mg/mL | 5,5′-Dichloro-1,1′-diphenylamino-3,3′-diethyl-10,12-ethylenethiatricarbocyanine Perchlorate | 0.1 mg/mL | 4:1 | THF (0.216 μm CML) | −0.128 nA (0.00057%) | (670 nm) |
| 77. Tetrakis(phenylthio) Phthalocyanine | 0.34 mg/mL | Silicon 2,3-Napthalocyanine bis(dimethylhexylvinylsilyl oxide) | 0.1 mg/mL | 4:1 | THF (0.216 μm CML) | −0.374 nA (0.00057%) | (670 nm) |
| 78. Tetrakis(phenylthio) Phthalocyanine | 0.28 mg/mL | 5,5′-Dichloro-1,1′-diphenylamino-3,3′-diethyl-10,12-ethylenethiatricarbocyanine Perchlorate | 0.1 mg/mL | 4:1 | THF (0.216 μm CML) | −0.109 nA (0.00057%) | (670 nm) |
| 79. (E,E)-3,5-bis-(4-phenyl-1,3-butadienyl)-4,4-difluoro-4-bora-3a,4a-diazo-s-indacene | 0.24 mg/mL | Tin Napthalocyanine [1,4-octabutoxy]$_4$Cl$_2$ | 0.1 mg/mL | 4:1 | THF (0.216 μm CML) | −1.724 nA (0.00057%) | (670 nm) |
| 80. Tetrakis(4-cumylphenoxy) Phthalocyanine | 0.36 mg/mL | Tin Napthalocyanine [1,4-octabutoxy]$_4$Cl$_2$ | 0.1 mg/mL | 4:1 | THF (0.216 μm CML) | −0.162 nA (0.00057%) | (670 nm) |
| 81. Tetrakis(phenylthio) Phthalocyanine | 0.26 mg/mL | Tin Napthalocyanine [1,4-octabutoxy]$_4$Cl$_2$ | 0.1 mg/mL | 4:1 | THF (0.216 μm CML) | −0.061 nA (0.00057%) | (670 nm) |
| 82. Germanium Phthalocyanine $(OH)_2(t-Bu)_4$ | 0.42 mg/mL | 5,5′-Dichloro-1,1′-diphenylamino-3,3′-diethyl-10,12-ethylenethiatricarbocyanine Perchlorate | 0.1 mg/mL | 4:1 | THF (0.216 μm CML) | −0.109 nA (0.00057%) | (670 nm) |

-continued

| DONOR DYE | LOADING CONC. (mg/mL) | ACCEPTOR DYE | LOADING CONC. mg/mL | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 83. Germanium Phthalocyanine $(OH)_2(t-Bu)_4$ | 0.22 mg/mL | Tin Napthalocyanine [1,4-octabutoxy]$_4$Cl$_2$ | 0.1 mg/mL | 4:1 | THF (0.216 μm CML) | −0.045 nA (0.00057%) | (670 nm) |
| 84. Germanium Phthalocyanine $(OH)_2(t-Bu)_4$ | 0.2 mg/mL | Tin Napthalocyanine [1,4-octabutoxy]$_4$Cl$_2$ | 0.1 mg/mL | 4:1 | THF (0.216 μm CML) | −0.042 nA (0.00057%) | (670 nm) |
| 85. Germanium Phthalocyanine $(Cl)_2(t-Bu)_4$ | 0.42 mg/mL | 5,5'-Dichloro-1,1'-diphenylamino-3,3'-diethyl-10,12-ethylenethiatricarbocyanine Perchlorate | 0.1 mg/mL | 4:1 | THF (0.216 μm CML) | −0.081 nA (0.00057%) | (670 nm) |
| 86. Germanium Phthalocyanine $(Cl)_2(t-Bu)_4$ | 0.22 mg/mL | Tin Napthalocyanine [1,4-octabutoxy]$_4$Cl$_2$ | 0.1 mg/mL | 4:1 | THF (0.216 μm CML) | −0.052 nA (0.00057%) | (670 nm) |
| 87. Germanium Phthalocyanine $(Cl)_2(t-Bu)_4$ | 0.2 mg/mL | Tin Napthalocyanine [1,4-octabutoxy]$_4$(OSiEt$_3$)$_{22}$ | 0.1 mg/mL | 4:1 | THF (0.216 μm CML) | −0.050 nA (0.00057%) | (670 nm) |
| 88. (E,E)-3,5-bis-(4-phenyl-1,3-butadienyl)-4,4-difluoro-4-bora-3a,4a-diazo-s-indacene | 0.16 mg/mL | Silicon 2,3-Naphthalocyanine bis(dimethylhexylvinylsilyl oxide) + 5,5'-Dichloro-1,1'-diphenylamino-3,3'-diethyl-10,12-ethylenethiatricarbocyanine Perchlorate | 0.1 mg/mL  0.072 mg/mL | 4:1:1 | THF (0.216 μm CML) | −0.315 nA (0.00057%) | (670 nm) |

We claim:

1. A loadable particle comprising an energy donor as a first component and an energy acceptor as a second component positioned in said particle at an energy exchanging distance from one another, wherein the two components have a stokes shift of greater than or equal to 50 nm, wherein said first component has an excitation wavelength greater than approximately 550 nm and said second component has an emission wavelength greater than approximately 680 nm, said particle having bound on its surface, a protein, polypeptide, nucleic acid, nucleotide or protein containing ligand analogue.

2. A loadable particle comprising an energy donor as a first component and a fluorescent dye as a second component positioned in said particle at an energy exchanging distance from one another, wherein said second component has an emission wavelength greater than approximately 680 nm, and wherein said first component is phthalocyanine substituted with at least one axial ligand and the two components have a stokes shift of greater than or equal to 50 nm.

3. A loadable particle comprising an energy donor as a first component and a fluorescent dye as a second component positioned in said particle at an energy exchanging distance from one another, wherein said second component has an emission wavelength greater than approximately 680 nm, and wherein said second component is phthalocyanine substituted with at least one axial ligand and the two components have a stokes shift of greater than or equal to 50 nm.

4. A loadable particle comprising an energy donor as a first component and a fluorescent dye as a second component positioned in said particle at an energy exchanging distance from one another, wherein said second component has an emission wavelength greater than approximately 680 nm, and wherein said first component is naphthalocyanine substituted with at least one axial ligand and the two components have a stokes shift of greater than or equal to 50 nm.

5. A loadable particle comprising an energy donor as a first component and a fluorescent dye as a second component positioned in said particle at an energy exchanging distance from one another, wherein said second component has an emission wavelength greater than approximately 680 nm, and wherein said second component is naphthalocyanine and the two components have a stokes shift of greater than or equal to 50 nm.

6. A loadable particle comprising an energy donor as a first component and a fluorescent dye as a second component positioned at an energy exchanging distance from one another, wherein said second component has an emission wavelength greater than approximately 680 nm, and wherein said first component is phthalocyanine substituted with at least one axial ligand and said second component is naphthalocyanine substituted with at least one axial ligand and the two components have a stokes shift of greater than or equal to 50 nm.

7. A particle loadable comprising an energy donor as a first component and a fluorescent dye as a second component positioned at an energy exchanging distance from one another, wherein said first component is a salt of trans-4-[4-(Dibutylamino)Styryl]-1-methyl pyridine and said second component is Silicon phthalocyanine bis (dimethylvinylsilyloxide) and the two components have a Stokes shift of greater than or equal to 50 nm.

8. A particle loadable comprising an energy donor as a first component and a fluorescent dye as a second component positioned at an energy exchanging distance from one another, wherein said first component is a salt of trans-4-[4-(Dibutylamino)Styryl]-1-methyl pyridine and said second component is Silion 2,3-Naphthalocyanine bis (dimethylvinylsilyloxide) and the two components have a Stokes shift of greater than or equal to 50 nm.

9. A loadable particle comprising an energy donor as a first component and a fluorescent dye as a second component positioned at an energy exchanging distance from one another, wherein said second component has an emission wavelength greater than approximately 680 nm, and wherein said first component is a salt of trans-4-[4-(Dibutylamino) Styryl]-1-methyl pyridine and said second component is a salt of 1,1-Dihexyl 3,3,3',3',-tetramethylindodicarbocyanine and the two components have a stokes shift of greater than or equal to 50 nm.

10. A loadable particle comprising an energy donor as a first component and a fluorescent dye as a second component positioned at an energy exchanging distance from one another, wherein said first component is Meso-tetra-2-aminophenyl porphine and said second component is Silicon phthalocyanine bis(dimethylvinylsilyloxide) and the two components have a Stokes shift of greater than or equal to 50 nm.

11. A loadable particle comprising an energy donor as a first component and a fluorescent dye as a second component positioned at an energy exchanging distance from one another, wherein said second component has an emission wavelength greater than approximately 680 nm, and wherein said first component is Meso-tetra-2-aminophenyl porphine and said second component is a salt of 1,1-Dihexyl 3,3,3', 3',-tetramethylindodicarbocyanine and the two components have a stokes shift of greater than or equal to 50 nm.

12. A particle loadable comprising an energy donor as a first component and a fluorescent dye as a second component positioned at an energy exchanging distance from one another, wherein said first component is Meso-tetra-2-dimethylaminophenyl porphine and said second component is Silicon phthalocyanine bis(dimethylvinylsilyloxide) and the two components have a Stokes shift of greater than or equal to 50 nm.

13. A particle comprising an energy donor as a first component and fluorescent dye as a second component positioned at an energy exchanging distance from one another, wherein said first component a salt of 3-Ethyl-3'-ethyl carboxyethyl thiacarbocyanine and said second component is Silicon 2,3-Napthalocyanine bis(dimethylvinylsilyloxide) and the two components have a Stokes shift of greater than or equal to 50 nm.

14. A particle loadable comprising an energy donor as a first component and a fluorescent dye as a second component positioned at an energy exchanging distance from one another, wherein said first component is a salt of 1,1'-Dioctadecyl-3,3,3',3'-tetramethlyindodicarbocyanine and said second component is Silicon 2,3-Naphthalocyanine bis(dimethylvinylsilyloxide) and the two components have a Stokes shift of greater than or equal to 50 nm.

15. A particle loadable comprising an energy donor as a first component and a fluorescent dye as a second component positioned at an energy exchanging distance from one another, wherein said first component is a salt of 1,1'-Diethyl-3,3,3',3'-tetramethylindodicarbocyanine and said second component is Silicon 2,3-Naphthalocyanine bis (dimethylvinylsilyloxide) and the two components have a Stokes shift of greater than or equal to 50 nm.

16. A particle loadable comprising an energy donor as a first component and a fluorescent dye as a second component positioned at an energy exchanging distance from one another, wherein said first component is a salt of 1,1'-Dihexyl-3,3,3',3'-tetramethlyindodicarbocyanine and said second component is Silicon 2,3-Naphthalocyanine bis (dimethylvinylsilyloxide) and the two components have a Stokes shift of greater than or equal to 50 nm.

17. A particle loadable comprising an energy donor as a first component and a fluorescent dye as a second component positioned at an energy exchanging distance from one another, wherein said first component is a salt of 3,3-Diethyl thiatricarbocyanine and said second component is Silicon 2,3-Naphthalocyanine bis(dimethylvinylsilyloxide) and the two components have a Stokes shift of greater than or equal to 50 nm.

18. A particle loadable comprising an energy donor as a first component and a fluorescent dye as a second component positioned at an energy exchanging distance from one another, wherein said first component is a salt of 3,3-Dipropyl thiatricarbocyanine and said second component is Silicon 2,3-Naphthalocyanine bis(dimethylvinylsilyloxide) and the two components have a Stokes shift of greater than or equal to 50 nm.

19. A particle loadable comprising an energy donor as a first component and a fluorescent dye as a second component positioned at an energy exchanging distance from one another, wherein said first component is a salt of 1,9-Dimethylmethylene blue and said second component is Silicon 2,3-Naphthalocyanine bis(dimethylvinylsilyloxide).

20. A loadable particle comprising an energy donor as a first component and a fluorescent dye as a second component positioned at an energy exchanging distance from one another, wherein said first component is a salt of N,N-Di(3-trimethylammoniumpropyl)thia-dicarbocyanine and said second component is Silicon 2,3-Naphthalocyanine bis (dimethylvinylsilyloxide) and the two components have a Stokes shift of greater than or equal to 50 nm.

21. A particle loadable comprising an energy donor as a first component and a fluorescent dye as a second component positioned at an energy exchanging distance from one another, wherein said first component is a salt of 1,1',3,3, 3',3'-Hexamethylindotricarbocyanine and said second component is Silicon 2,3-Naphthalocyanine bis (dimethylvinylsilyloxide) and the two components have a Stokes shift of greater than or equal to 50 nm.

22. A particle loadable comprising an energy donor as a first component and a fluorescent dye as a second component positioned at an energy exchanging distance from one another, wherein said first component is a salt of N-(3-Triethlylammoniumpropyl)-4-(4-(p-dibutylaminophenyl) butadienyl)pyridine and said second component is Silicon 2,3-Naphthalocyanine bis(dimethylvinylsilyloxide) and the two components have a Stokes shift of greater than or equal to 50 nm.

23. A particle loadable comprising an energy donor as a first component and a fluorescent dye as a second component positioned at an energy exchanging distance from one another, wherein said first component is a salt of 1,1',3,3, 3',3'-Hexamethyl-4,4'-5,5'-dibenzo-2,2'indotricarbocyanine and said second component is Silicon Naphthalocyanine bis(dimethylvinylsilyloxide) and the two components have a Stokes shift of greater than or equal to 50 nm.

24. A particle loadable comprising an energy donor as a first component and a fluorescent dye as a second component positioned at an energy exchanging distance from one another, wherein said first component is Fluorescein and said second component is Silicon Phthalocyanine bis (dimethylvinylsilyloxide) and the two components have a Stokes shift of greater than or equal to 50 nm.

25. A particle loadable comprising an energy donor as a first component and a fluorescent dye as a second component positioned at an energy exchanging distance from one another, wherein said first component is Chlorophyll and said second component is Silicon 2,3-Naphthalocyanine bis(dimethylvinylsilyloxide) and the two components have a Stokes shift of greater than or equal to 50 nm.

26. A particle loadable comprising an energy donor as a first component and a fluorescent dye as a second component positioned at an energy exchanging distance from one another, wherein said first component is Chlorophyll and said second component is Silicon phthalocyanine bis (dimethylvinylsilyloxide) and the two components have a Stokes shift of greater than or equal to 50 nm.

27. A particle comprising an energy donor as a first component and second and third components comprising 2 fluorescent dyes positioned at an energy exchanging distance from one another, wherein said first component is a salt of trans-4-[4(Dibutylamino)styryl]-1-methyl pyridine and one of dyes is selected from the group consisting of Silicon phthalocyanine bis (dimethylpentafluorophenylsilyloxide) and Silicon phthalocyanine bis(dimethlylvinylsilyloxide).

28. A particle comprising an energy donor as a first component and 3 fluorescent dyes positioned at an energy exchanging distance from one another, wherein said first component is a salt of trans-4-[4(Dibutylamino)styryl]-1-methyl pyridine and said three dyes are selected from the group consisting of Silicon phthalocyanine bis (trihexylsilyloxide), Silicon phthalacyanine bis (dimethylpentafluorophenylsilyloxide), Silicon phthalocyanine bis(dimethylvinylsilyloxide).

29. A loadable particle comprising an energy donor as a first component and a fluorescent dye as a second component positioned at an energy exchanging distance from one another, wherein said second component has an emission wavelength greater than approximately 680 nm, and wherein said first component is a styryl dye and said second component is phthalocyanine substituted with at least one axial ligand and the two components have a stokes shift of greater than or equal to 50 nm.

30. A loadable particle comprising an energy donor as a first component and a fluorescent dye as a second component positioned at an energy distance from one another, wherein said second component has an emission wavelength greater than approximately 680 nm, and wherein said first component is a styryl dye and said second component is naphthalocyanine substituted with at least one axial ligand and the two components have a stokes shift of greater than or equal to 50 nm.

31. A loadable particle comprising an energy donor as a first component and a fluorescent dye as a second component positioned at an energy exchanging distance from one another, wherein said second component has an emission wavelength greater than approximately 680 nm, and wherein said first component is a phenylbutadienyl dye and said second component is phthalocyanine substituted with at least one axial ligand and the two components have a stokes shift of greater than or equal to 50 nm.

32. A loadable particle comprising an energy donor as a first component and a fluorescent dye as a second component positioned at an energy exchanging distance from one another, wherein said second component has an emission wavelength greater than approximately 680 nm, and wherein said first component is a phenylbutadienyl dye and said second component is naphthalocyanine substituted with at least one axial ligand and the two components have a stokes shift of greater than or equal to 50 nm.

33. A loadable particle comprising an energy donor as a first component and a fluorescent dye as a second component positioned at an energy exchanging distance from one another, wherein said second component has an emission wavelength greater than approximately 680 nm, and wherein said first component is a phenylhexatrienyl dye and said second component is phthalocyanine substituted with at least one axial ligand and the two components have a stokes shift of greater than or equal to 50 nm.

34. A loadable particle comprising an energy donor as a first component and a fluorescent dye as a second component positioned at an energy exchanging distance from one another, wherein said second component has an emission wavelength greater than approximately 680 nm, and wherein said first component is a phenylhexatrienyl dye and said second component is naphthalocyanine substituted with at least one axial ligand and the two components have a stokes shift of greater than or equal to 50 nm.

35. A loadable particle comprising an energy donor as a first component and a fluorescent dye as a second component positioned at an energy exchanging distance from one another, wherein said second component has an emission wavelength greater than approximately 680 nm, and wherein said first component is a porphine dye and said second component is phthalocyanine substituted with at least one axial ligand and the two components have a stokes shift of greater than or equal to 50 nm.

36. A loadable particle comprising an energy donor as a first component and a fluorescent dye as a second component positioned at an energy exchanging distance from one another, wherein said second component has an emission wavelength greater than approximately 680 nm, and wherein said first component is a porphine dye and said second component is naphthalocyanine substituted with at least one axial ligand and the two components have a stokes shift of greater than or equal to 50 nm.

37. A loadable particle comprising an energy donor as a first component and a fluorescent dye as a second component positioned at an energy exchanging distance from one another, wherein said second component has an emission wavelength greater than approximately 680 nm, and wherein said first component is a carbocyanine dye and said second component is phthalocyanine substituted with at least one axial ligand and the two components have a stokes shift of greater than or equal to 50 nm.

38. A loadable particle comprising an energy donor as a first component and a fluorescent dye as a second component positioned at an energy exchanging distance from one another, wherein said second component has an emission wavelength greater than approximately 680 nm, and wherein said first component is a carbocyanine dye and said second component is naphthalocyanine substituted with at least one axial ligand and the two components have a stokes shift of greater than or equal to 50 nm.

39. A loadable particle in accordance with any of claims 1–11, 20 or 29–38, wherein said loadable particle is latex.

40. A loadable particle in accordance with any of claims 1–11, 20, or 29–38 wherein said particle comprises two or more dye molecules having approximately the same excitation and emission wavelengths, whereby quenching is decreased and fluorescence intensity is increased by the combination of said dye molecules.

41. The particle of any one of claims 1–26 or 29–38 comprising at least one additional fluorescent dye as a third component, said third component exhibiting in the particle approximately the same excitation and emission wavelengths as said second component, whereby quenching is decreased and fluorescence intensity is increased by the combination of said second and said additional component (s).

42. The particle of claim 27 comprising at least one additional fluorescent dye as a fourth component, said fourth component exhibiting in the particle approximately the same excitation and emission wavelengths as one of said second or third components, whereby quenching is decreased and fluorescence intensity is increased by the combination of said second or third and said fourth components.

43. The loadable particle of any of claims 1–11, 20, or 29–38 comprising at least one additional fluorescent dye as a third component, said third component exhibiting in the particle approximately the same excitation and emission wavelengths as said second component, whereby quenching is decreased and fluorescence intensity is increased by the combination of said second and said additional component (s).

44. A loadable particle in accordance with claim 1 wherein the energy donor and/or the energy acceptor are incorporated inside the particle.

45. A loadable particle in accordance with claim 1 wherein the energy donor and/or the energy acceptor are incorporated at the surface of the particle.

46. A loadable particle in accordance with claim 40 wherein the dye molecules having approximately the same excitation and emission wavelengths are incorporated inside the particle.

47. A loadable particle in accordance with claim 40 wherein the dye molecules having approximately the same excitation and emission wavelengths are incorporated at the surface of the particle.

48. A latex particle comprising an energy donor as a first component and an energy acceptor as a second component positioned in said particle at an energy exchanging distance from one another, wherein; (1) said first component has an excitation wavelength greater than approximately 550 nm and said second component has an emission wavelength greater than approximately 680 nm; (2) said first component is a fluorescent dye and said second component is phthalocyanine-substituted with at least one axial ligand; and (3) the two components have a Stokes shift of greater than or equal to 50 nm.

49. A particle comprising an energy donor as a first component and an energy acceptor as a second component positioned in said particle at an energy exchanging distance from one another, wherein: (1) said first component has an excitation wavelength greater than approximately 550 nm and said second component has an emission wavelength, greater than approximately 680 nm; (2) said second component is phthalocyanine substituted with at least one axial ligand; and (3) the two components have a Stokes shift of greater than or equal to 50 nm.

50. A latex particle comprising an energy donor as a first component and an energy acceptor as a second component positioned in said particle at an energy exchanging distance from one another, wherein: (1) said first component is a fluorescent dye having an excitation wavelength greater than approximately 550 nm and said second component is a fluorescent dye having an emission wavelength greater than approximately 680 nm; and (2) the two components have a Stokes shift of greater than or equal to 50 nm.

51. A particle in accordance with any of claims 7, 8, 12–19, or 21–28 wherein said particle is selected from the group consisting of silica, alumina, liposomes and colloids.

52. A particle in accordance with any of claims 7, 8, 12–19, or 21–28, wherein said particle is latex.

53. An improved particle in accordance with any of claims 7, 8, 12–19, or 21–28 wherein the improvement comprises adding to said particle two or more dye molecules having approximately the same excitation and emission wavelengths, whereby quenching is decreased and fluorescence intensity is increased by the combination of said dye molecules.

54. A particle for assaying analytes in a biological medium comprising an energy donor as a first component and an energy acceptor as a second component positioned in said particle at an energy exchanging distance from one another, wherein said first component has an excitation wavelength greater than about 600 nm, said second component has at least one emission wavelength other than the intrinsic fluorescent wavelength of the biological medium, and the two components have a Stokes shift of greater than or equal to 50 nm, said particle having bound on its surface, a protein, polypeptide, nucleic acid, ligand analogue, nucleotide or a protein-containing ligand analogue.

55. A particle comprising an energy donor as a first component, an energy acceptor as a second component, and at least one additional energy acceptor as a third component, wherein: (1) said first component and said second component are positioned in said particle at an energy exchanging distance from one another; (2) said first component has an excitation wavelength greater than approximately 550 nm and said second component has an emission wavelength greater than approximately 680 nm; (3) said first component and said second component have a Stokes shift of greater than or equal to 50 nm; and (4) said third component is a fluorescent dye, said third component exhibiting in the particle approximately the same excitation and emission wavelengths as said second component, whereby quenching is decreased and fluorescence intensity is increased by the combination of said second and said third component.

56. A particle comprising an energy donor as a first component, an energy acceptor having an absorbance wavelength approximately equal to the emission wavelength of said first component as a second component, and at least one additional energy acceptor as a third component, wherein said first component and said second component are positioned in said particle at an energy exchanging distance from one another, wherein said first component and said second component have a Stokes shift of greater than or equal to 50 nm, and wherein said third component is a fluorescent dye exhibiting in the particle approximately the same excitation and emission wavelengths as said second component, whereby quenching is decreased and fluorescence intensity is increased by the combination of said second and said third component.

57. A loadable particle in accordance with any of claims 1–11, 20, or 29–38 wherein said particle is selected from the group consisting of silica, alumina, liposomes and colloids.

* * * * *